US007211408B2

(12) United States Patent
Rogers et al.

(10) Patent No.: US 7,211,408 B2
(45) Date of Patent: May 1, 2007

(54) RECOMBITOPE PEPTIDES

(75) Inventors: Bruce L. Rogers, Belmont, MA (US);
Jay P. Morgenstern, Boston, MA (US);
Julian F. Bond, Weymouth, MA (US);
Richard D. Garman, Arlington, MA
(US); Julia L. Greenstein, West
Newton, MA (US); Mei-Chang Kuo,
Palo Alto, CA (US); Malcolm Morville,
Shrewsbury, MA (US)

(73) Assignee: Merck Patent GmbH, Darmstadt (DE)

( * ) Notice: Subject to any disclaimer, the term of this patent is extended or adjusted under 35 U.S.C. 154(b) by 304 days.

(21) Appl. No.: 10/463,113

(22) Filed: Jun. 16, 2003

(65) Prior Publication Data

US 2004/0057959 A1 Mar. 25, 2004

Related U.S. Application Data

(63) Continuation of application No. 08/464,363, filed on Jun. 5, 1995, now abandoned, which is a continuation of application No. 07/807,529, filed on Dec. 13, 1991, now Pat. No. 5,547,669, which is a continuation-in-part of application No. 07/662,276, filed on Feb. 28, 1991, now abandoned, which is a continuation-in-part of application No. 07/431,565, filed on Nov. 3, 1989, now abandoned.

(30) Foreign Application Priority Data

Nov. 2, 1990 (WO) ............... PCT/US90/06548

(51) Int. Cl.
*G01N 33/00* (2006.01)
*C12N 15/09* (2006.01)
*C07K 1/00* (2006.01)

(52) U.S. Cl. ............... 435/7.24; 435/69.3; 435/69.7; 530/324; 530/325; 530/326; 530/806; 530/858; 530/868

(58) Field of Classification Search ............... 530/324, 530/325, 326, 806, 858, 868; 435/69.3, 69.7, 435/7.24, 513, 275.1
See application file for complete search history.

(56) References Cited

U.S. PATENT DOCUMENTS 4,906,564 A  3/1990  Lyon et al.
5,114,713 A  5/1992  Sinigaglia
5,126,399 A  6/1992  Arlinghaus et al.

FOREIGN PATENT DOCUMENTS

EP  0 304 279 B1  11/1997
WO  WO 91/06571 A1  5/1991

OTHER PUBLICATIONS

Bach et al. *Immunology* 2nd Ed. pp. 349-350.

Beachey, E.H. et al. "Opsonic antibodies evoked by hybrid peptide copies of types 5 and 24 streptococcal M proteins synthesized in tandem." *J. Exp. Med.* 163:1451-1458 (1986).
Berzofsky, J.A. (1988)"Structural Basis of Antigen Recognition by T Lymphocytes Implications for Vaccines" *J. Clin. Invest.* 82:1811-1817.
Brett, S.J. et al. (1989) "Different Pattern of T Cell Recognition of the 65-KDA Mycobacterial Antigen Following Immunization With the Whole Protein or Peptides" *Eur. J. Immunol.* 19:1303-1310.
Chua et al., (1990) "Expression of Dermatophagoides pteronyssinus Allergen, Der pII, in *Escherichia coli* and the Binding Studies with Human IgE" *Int. Arch. Allergy Appl. Immunol.* 91:124-129.
Greene, W.K., et al. (1990) "Antigenic Analysis of Group I House Dust Mite Allergens Using Random Fragments of Der p I Expressed by Recombinant DNA Libraries" *Int. Arch. Allergy Exp. Immunol.* 92:30-38.
Gurka et al. (1989) "Allergen-Specific human T cell clones: Derivation, specificy, and activation requirements" *J. Allergy Clin Immunol.* 83:945-954.
Horiuchi, T. et al. (1988) "Core Sequence of Two Separable Terinus Sites of the R6K Plasmid that Exhibit Polar Inhibition of Replicaiton I a 20 bp Inverted Repeat" *Cell* 54:515-523.
Lai, M. et al. (1987) "T Lymphocyte Response to Bacteriophage Repressor cl Protein" The *Journal of Immunology* 139:3973-3980.
Lamb, J. et al. (1987) Mapping of T cell epitopes using recombinant antigens and synthetic peptides *The EMBO Journal* 6(5):1245-1249.
Leiterman et al. (1984). "Cat allergen 1: biochemical . . . " *J. Allergy Clin. Immunol.* 74(2):147-153.
Londono, J.A. et al. (1990) "Secondary structure and immunogenicity of hybrid synthetic peptides derived from two *Plasmodium falciparum* pre-erythrocytic antigens." *Journal of Immunology* 145(5):1557-1563.
Michael, J.G. et al. (1990) "Modulation of the immune response to ragweed allergens by peptic fragments" *Clin. Exp. Allergy* 20:669-674.
Munesinghe, D.Y. et al. (1991) Immunogenicity of Multiple Antigen Peptides Map Containing T and B Cell Epitopes of the Repeat Region of the Plasmodium-Falciparum Circumsporozoite Protein *European Journal of Immunology* 21(12):3015-3020.

(Continued)

*Primary Examiner*—Christina Chan
*Assistant Examiner*—F. Pierre VanderVegt
(74) *Attorney, Agent, or Firm*—Lahive & Cockfield, LLP

(57) ABSTRACT

The present invention provides peptides having T cell stimulating activity termed recombitope peptides. Recombitope peptides of the invention preferably comprise at least two T cell epitopes derived from the same or from different protein antigens, and more preferably comprise at least two regions, each region preferably having human T cell stimulating activity and each region comprising at least one T cell epitope derived from a protein antigen. Recombitope peptides of the invention can be derived from protein allergens, autoantigens, or other protein antigens. The invention also provides methods of diagnosing sensitivity to a protein allergen or other protein antigen in an individual, methods to treat such sensitivity and therapeutic compositions comprising one or more recombitope peptides. The invention further provides methods for designing recombitope peptides of the invention where the protein antigen to which the individual is sensitive has unknown or ill-defined T cell epitopes.

15 Claims, 19 Drawing Sheets

OTHER PUBLICATIONS

O'Hehir, R. et al. (1991) "The Specificity and Regulation of T-Cell Responsiveness to Allergens" *Annu. Rev. Immunol.* 9:67-95.

Ota, K. et al. (1990) "T-Cell Recognition of an Immunodominant Myelin Basic Protein Epitope In Multiple Sclerosis" *Nature* 346:183-187.

Perez, M. et al. (1990) "cDNA Cloning and Immunological Characterization of the Rye Grass Allergen Lol p I*" *The Journal of Biological Chemistry* 265(27):16210-16215.

Rogers, B.L. et al. (1991) "Genomic Structure and Expression in Cat Tissues" *J. Allergy Clin. Immunol.* 87(1 pt 2):327, abstract 750.

Rosenwasser et al. (Mar. 5, 1991) Molecular Biology of Allergen Characterization, Postgraduate Education Course Syllabus, AAAI Metting, pp. 159-169.

Rothbard et al., (1988) "A sequence pattern commn to T cell epitopes" *EMBO J.* 7(1):97-100.

Roux et al. "Mutation of isoleucine 747 by a threonine alters the ligand responsiveness of the human glucocorticoid receptor." *Molecular Endocrinology* 10:1214-1226 (1996).

Shastri, N. et al. (1986) "Ia Molecule-Associated Selectivity in T Cell Recognition of a 23-Amino-Acid Peptide of Lysozyme" (1986) *J. Exp. Med.* 164:882-896.

Shen, S. H. et al. (1984) "Multiple joined genes prevent product degradation in *Escherichia coli*" *Proc. Natl. Acad. Sci. USA* 81:4627-31.

Shimonkevitz, R., et al. (1984) "Antigen Recognition by H-2-Restrictred T Cells" *J. of Immunology* 133(4):2067-2074.

Simpson et al. (1989) "Structural studies on the allergen Der p1 . . ." *Prot. Seq. Data Anal.* 2:17-21.

Sinigaglia, F. et al. (1991) "Section of T cell Epitopes and Vaccine Engineering" Meth. Enzynology, vol. 203. Molecular design and modeling: Concepts and Applications, Part B: Antibodies and Antigens, Nucleic Acids, Polysaccharides, and Drugs. (Book, pp. 370-386).

Stewart et al. (Sep. 1989) "Epitope Mapping Analysis of the Major Mite Allergens Using Synthetic Peptides" Proc. of Workshop XIVth Congress Europ. Acad. Allergy and Clinical Immunology, Berlin.

Tam, J.P. (1988) "Synthetic peptide vaccine design: Synthesis and properties of a high-density multiple antigenic peptide system" *Proc. Natl. Acad. Science USA* 85:5409-5413.

Thomas et al. (Sep. 1989) "Proceedings of Workshop XIVth Congress Europ. Acad. allergy and Clinical Immunology", Berlin.

V.C. Schad et al., (1991) *Seminars in Immunology* 3:217-224.

Yssel et al. (Sep. 24, 1990)"T cell activation by allergen derived synthetic peptides" Session 4: Immunity to Peptides, Conference on T Cell Activation in health and Disease, Trinity College, Oxford, U.K.

Zamvil, Scott et al. (1986) "T-Cell epitope of the autoantigen myelin basic protein that induces encephalomyelitis" *Nature* 324:258-260.

LEADER A
              M K G A R V L V L L W A A L L L I W G G N C
CTGCATC ATGAAGGGGGCTCGTGTTCTCGTGCTTCTCTGGCTGCCTTGCTCTTGATCTGGGGTGGAAATTGT
GGCCTGGCGGTGCTGCTCCTGGAAAAGG ATGTTAGACGCAGCCCTCCACCTGCCCTGCCCTACTGTTGCGGCCACAGCAGATTGT

LEADER B
                                    M L D A A L P P C P T V A A T A D C

E I C P A V K R D V D L F L T G T P D E Y V E Q V A Q Y K A
GAAATTGCCCAGCCGGTGAAGAGAGGGATGTTGACCTATTCCTGACGGGAACCCCCGACGAATATGTTGAGCAAGTGGCACAATACAAAGCA

L P V V L E N A R I L K N C V D A K M T E E D K E N A L S L
CTACCTGTAGTATTGGAAAATGCCAGAATACTGAAGAATGCCGTTGATGCAAAAATGACAGAAGAGGATAAGGAGAATGCTCTCAGCTTG

L D K I Y T S P L C -
CTGGACAAAATATACACAAGTCCCTCTGTGTTAAAGGAGCCATCACTGCCAGGAGCCCTAAGGAAGCCACTGAACTGATCACTAAGTAGTCT

CAGCAGCCTGCCATGTCCAGGTGTCTTACTAGAGGATTCTTGCAATTCAAACAAAAAAAAAAA

Fig. 1

```
                                                                                TGACACGATGAGGGGGCACTGCTTGTGCTGGCATTGCTGGTGACCCAAGCGCTGGGC  58
                                                                                 M  R  G  A  L  L  V  L  A  L  L  V  T  Q  A  L  G
                                                                                -17    -15             -10              -5

GTCAAGATGGCGGAAACTTGCCCCATTTTTATGACGTCTTTTTTGCGGTGGCCAATGGAAATGAATTACTGTTGGACTGTCCCTCACA  148
 V  K  M  A  E  T  C  P  I  F  Y  D  V  F  F  A  V  A  N  G  N  E  L  L  D  L  S  L  T
    1              5              10             15             20             25            30

AAAGTCAATGCTACTGAACCAGAGAACAGCCATGAAAAAATCCAGGATTGCTACGTGGAGAACGGACTCATATCCAGGGTCTTGGAT  238
 K  V  N  A  T  E  P  E  R  T  A  M  K  K  I  Q  D  C  Y  V  E  N  G  L  I  S  R  V  L  D
              35             40             45             50             55             60

GGACTAGTCATGACAATCAGCTCCAAAGATTGCATGGGTGAAGCAGTTCAGAACACCGTAGAAGATCTCAAGCTGAACACTTTG  328
 G  L  V  M  T  T  I  S  S  K  D  C  M  G  E  A  V  Q  N  T  V  E  D  L  K  L  N  T  L
      65             70             75             80             85             90

GGGAGATGAATTTGCCACTGATGCCCCTTCTGAGCCCCATCCTCCTGCCCCTGTTCTTTACACCTAAAGCTGGAATCCAGACACCTGTCC  418
 G  R  -

TCACCTAATTCACTCTCAATCAGGCTGACTAGAATAAAAATAACTGCATCTTAAAAAAAAAAAAAAA  485
```

Fig. 2

| PEPTIDE NAME | SEQUENCE |
|---|---|
| X | KRDVDLFLTGTPDEYVEQVAQYKALPV |
| Y | KALPVVLENARILKNCVDAKMTEEDKE |
| Z | FFAVANGNELLDLSLTKVNATEPER |
| A | EEDKENALSLLDKIYTSPL |
| B | MGEAVQNTVEDLKLNTLGR |
| C | TEEDKENALSLLDKIYTSPL |

Fig. 4

```
       BAM HI
C  5' GGGGATCCAAAGCTCTGCCGGTTGTT 3'
       K  A  L  P  V  V

BAM HI
D  5' GGGGATCCAAAGCTCTGCCGGTTGTTCTGGAAAACGCTCGTATCCTGAAAAACTGCGTTGACGCTAAAATGACCGAA
       K  A  L  P  V  V  L  E  N  A  R  I  L  K  N  C  V  D  A  K  M  T  E
   GAAGACAAAGAA 3'
    E  D  K  E

E  3' CTTCTTCTGTTTCTTAAGAAGCGACAACGATTGCCATTGCTGACGACCTGGACAGAGAC 5'
       E  E  D  K  E  F  F  A  V  A  N  G  N  E  L  L  D  L  S  L

F  5' CTGGACCTGTCTCTGACCAAAGTTAACGCTACCGAACGT 3'
       L  D  L  S  L  T  K  V  N  A  T  E  P  E  R

G  3' TGGCTTGGCCTTGCATTGCACTGCAACTGGACAAGGACTGGCCATGGGGCCTG 5'
       T  E  P  E  R  R  K  R  D  V  D  L  F  L  T  G  T  P  D

H  5' ACCGGTACCCCGGACGAATACGTTGAACAGGTTGCTCAGTACAAAGCTCTGCCGGTTTAGTAGTCTAGACTGCAGAAG
       T  G  T  P  D  E  Y  V  E  Q  V  A  Q  Y  K  A  L  P  V  -  -  XBAI  PSTI
   CTTGGATCCCC 3'
    HINDIII ECORI
```

Fig. 7

I  3' CGAGACGGCCAAATCATCAGATCTGACGTCTTCGAACCTAGGGG 5'
        A   L   P   V   -   -  XBAI PSTI HINDIII ECORI

J  5' GGGGATCCGAAGAAGACAAAGAAAACGCTCTGTCTCTGCTG 3'
      BAM HI  E  E  D  K  E  N  A  L  S  L  L

K  3' GACAGAGACGACCTGTTTTAGATGTGGAGAGGCGACTTTCGAGACGGCCAACAAGACCTT 5'
        L   S   L   L   D   K   I   Y   T   S   P   L   K   A   L   P   V   V   L   E

L  3' CGAGTCATGTTTCGAGACGGCCAATACCCACTTCGACAAGTCTTGTGGCAACTT 5'
        A   Q   Y   K   A   L   P   V   M   G   E   A   V   Q   N   T   V   E

M  5' CAGAACACCCGTTGAAGACCTGAAACTGAATGTAACTGCAGAATTCCCC 3'
       Q  N  T  V  E  D  L  K  L  N  T  L  G  R  -        PST I ECORI

N  5' GGGGATCCGAAGAAGACAAAA 3'
      BAM HI  E  E  D  K

O  3' TGAAACCCCTCTACTTACATTGACGTCTTAAGGGG 5'
       T  L  G  R  -        PST I ECORI

Fig. 7 cont.

ATGGGTCACCACCACCACCACCACGAATTCCTGGTTCCGCGTGGATCC
M  G  H  H  H  H  H  H  E  F  L  V  P  R  G  S

AAAGCTCTGCCGGTTGTTCTGGAAAACGCTCGTATCCTGAAAAACTGC
K  A  L  P  V  V  L  E  N  A  R  I  L  K  N  C

GTTGACGCTAAAATGACCGAAGAAGACAAAGAATTCTTCGCTGTTGCT
V  D  A  K  M  T  E  E  D  K  E  F  F  A  V  A

AACGGTAACGAACTGCTGCTGGACCTGTCTCTGACCAAAGTTAACGCT
N  G  N  E  L  L  L  D  L  S  L  T  K  V  N  A

ACCGAACCGGAACGTAAACGTGACGTTGACCTGTTCCTGACCGGTACC
T  E  P  E  R  K  R  D  V  D  L  F  L  T  G  T

CCGGACGAATACGTTGAACAGGTTGCTCAGTACAAAGCTCTGCCGGTT
P  D  E  Y  V  E  Q  V  A  Q  Y  K  A  L  P  V

Fig. 8

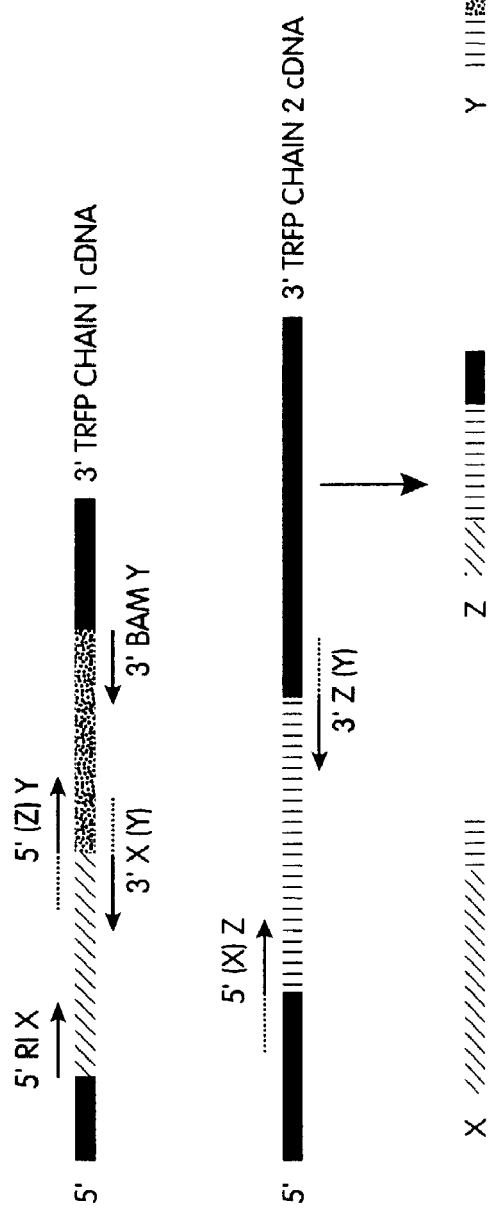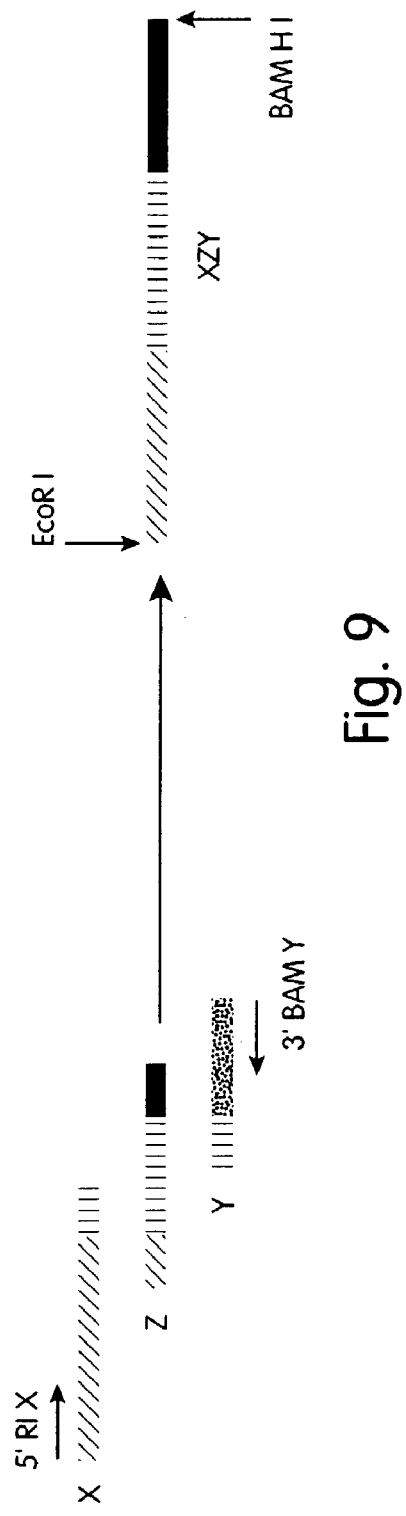
Fig. 9

5' PRIMERS

XZY CONSTRUCT

```
                         K   R   D   V   D   L
5' XRI     5'-GGGGAATTCAAGAGGGATGTTGACCTA-3'
                ECOR I           X

L   P   V │ F   F   A   V   A   N
5' (X) Z   5'-CTACCTGTA TTTTTTGCGGTGGCCAAT-3'
                        X     │         Z

P   E   R │ K   A   L   P   V   V
5' (Z) Y   5'-CCAGAGAGA AAGCACTACCTGTAGTA-3'
                        Z     │         Y
```

YXZ CONSTRUCT

```
                         K   A   L   P   V   V
5' YRI     5'-GGGGAATTCAAAGCACTACCTGTAGTA-3'
                ECOR I           Y

D   K   E │ K   R   D   V   D   L
5' (Y) X   5'-GATAAGGAG AAGAGGGATGTTGACCTA-3'
                        Y     │         X

L   P   V │ F   F   A   V   A   N
5' (X) Z   5'-CTACCTGTA TTTTTTGCGGTGGCCAAT-3'
                        X     │         Z
```

ZXY CONSTRUCT

```
                         F   F   A   V   A   N   G
5' ZRI     5'-GGGGAATTCTTTGCGGTGGCCAATGGA-3'
                ECOR I               Z

K   R   D   V   D   L   P
5' (Z) X   5'-AAGAGGGATGTTGACCTATTC-3'
                                    X
```

Fig. 10

3' PRIMERS

XZY CONSTRUCT

```
              αN  αA  αV  αA  αF  αF |αV  αP  αL  αA  αK  αY
3' X (Z)   5'-ATTGGCCACCGCAAAAAA TACAGGTAGTGCTTTGTA-3'
                          Z     |           X
              αL  αA  αK |αR  αE  αP  αE  αT  αA
3' Z (Y)   5'-TAGTGCTTT TCTCTCTGGTTCAGTAGC-3'
                     Y |              Z

αSTOPαE  αK  αD  αE  αE  αT
3' Y BAM   5'-GGGGATCCTTACTCCTTATCCTCTTCTGT-3'
              BAMH I                Y
```

YXZ CONSTRUCT

```
              αL  αD  αV  αD  αR  αK |αE  αK  αD  αE  αE  αT
3' Y (X)   5'-TAGGTCAACATCCCTCTT CTCCTTATCCTCTTCTGT-3'
                          X         |            Y
              αA  αF  αF |αV  αP  αL  αA  αK  αY
3' X (Z)   5'-CGCAAAAAA TACAGGTAGTGCTTTGTA-3'
                     Z |              X

αSTOPαR  αE  αP  αE  αT  αA
3' Z BAM   5'-GGGGATCCTTATCTCTCTGGTTCAGTAGC-3'
              BAMH I                Z
```

ZXY CONSTRUCT

```
              αL  αD  αV  αD  αR  αK |αR  αE  αP  αE  αT  αA  αN
3' Z (X)   5'-TAGGTCAACATCCCTCTT CTCTCTGGTTCAGTAGCATT-3'
                          X         |            Z
              αSTOPαE  αK  αD  αE  αE  αT  αM
3' Y BAM   5'-GGGGATCCTCACTCCTTATCCTCTTCTGTCAT-3'
              BAMH I                Y
```

Fig. 10 cont.

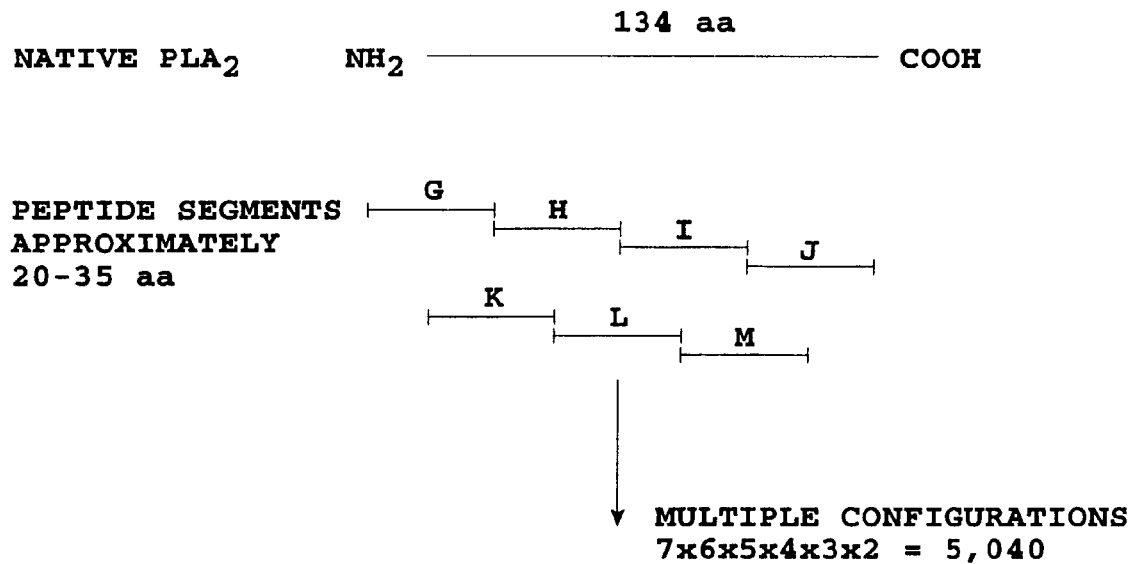
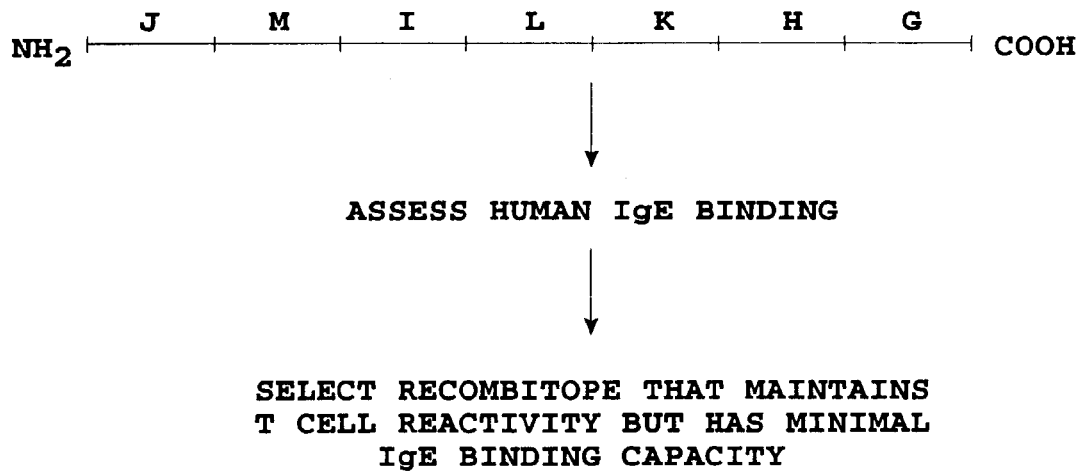
Fig. 12

SEQUENCE LISTING (1) GENERAL INFORMATION:

(iii) NUMBER OF SEQUENCES: 76

(2) INFORMATION FOR SEQ ID NO: 1:

(i) SEQUENCE CHARACTERISTICS:
          (A) LENGTH: 422 base pairs
          (B) TYPE: nucleic acid
          (C) STRANDEDNESS: single
          (D) TOPOLOGY: linear (ii) MOLECULE TYPE: cDNA (ix) FEATURE:
          (A) NAME/KEY: CDS
          (B) LOCATION: 8..286

(ix) FEATURE:
          (A) NAME/KEY: mat_peptide
          (B) LOCATION: 74..286

(xi) SEQUENCE DESCRIPTION: SEQ ID NO: 1:

```
CTGCATC ATG AAG GGG GCT CGT GTT CTC GTG CTT CTC TGG GCT GCC TTG         49
        Met Lys Gly Ala Arg Val Leu Val Leu Leu Trp Ala Ala Leu
        -22     -20             -15                 -10

CTC TTG ATC TGG GGT GGA AAT TGT GAA ATT TGC CCA GCC GTG AAG AGG         97
Leu Leu Ile Trp Gly Gly Asn Cys Glu Ile Cys Pro Ala Val Lys Arg
            -5                1               5

GAT GTT GAC CTA TTC CTG ACG GGA ACC CCC GAC GAA TAT GTT GAG CAA        145
Asp Val Asp Leu Phe Leu Thr Gly Thr Pro Asp Glu Tyr Val Glu Gln
        10              15              20

GTG GCA CAA TAC AAA GCA CTA CCT GTA GTA TTG GAA AAT GCC AGA ATA        193
Val Ala Gln Tyr Lys Ala Leu Pro Val Val Leu Glu Asn Ala Arg Ile
25              30              35              40

CTG AAG AAC TGC GTT GAT GCA AAA ATG ACA GAA GAG GAT AAG GAG AAT        241
Leu Lys Asn Cys Val Asp Ala Lys Met Thr Glu Glu Asp Lys Glu Asn
                45              50              55

GCT CTC AGC TTG CTG GAC AAA ATA TAC ACA AGT CCT CTG TGT TAAAGGAGCC     293
Ala Leu Ser Leu Leu Asp Lys Ile Tyr Thr Ser Pro Leu Cys
            60              65              70

ATCACTGCCA GGAGCCCTAA GGAAGCCACT GAACTGATCA CTAAGTAGTC TCAGCAGCCT      353

GCCATGTCCA GGTGTCTTAC TAGAGGATTC CAGCAATAAA AGCCTTGCAA TTCAAACAAA      413

AAAAAAAAA                                                             422
```

(2) INFORMATION FOR SEQ ID NO: 2:

(i) SEQUENCE CHARACTERISTICS:
          (A) LENGTH: 92 amino acids
          (B) TYPE: amino acid
          (D) TOPOLOGY: linear (ii) MOLECULE TYPE: protein (xi) SEQUENCE DESCRIPTION: SEQ ID NO: 2:

```
Met Lys Gly Ala Arg Val Leu Val Leu Leu Trp Ala Ala Leu Leu Leu
-22     -20             -15                 -10
```

```
Ile Trp Gly Gly Asn Cys Glu Ile Cys Pro Ala Val Lys Arg Asp Val
    -5                1               5                       10

Asp Leu Phe Leu Thr Gly Thr Pro Asp Glu Tyr Val Glu Gln Val Ala
                15              20              25

Gln Tyr Lys Ala Leu Pro Val Val Leu Glu Asn Ala Arg Ile Leu Lys
            30              35              40

Asn Cys Val Asp Ala Lys Met Thr Glu Glu Asp Lys Glu Asn Ala Leu
            45              50              55

Ser Leu Leu Asp Lys Ile Tyr Thr Ser Pro Leu Cys
60              65              70
```

(2) INFORMATION FOR SEQ ID NO: 3:

(i) SEQUENCE CHARACTERISTICS:
        (A) LENGTH: 428 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: mat_peptide
        (B) LOCATION: 80..292

(ix) FEATURE:
        (A) NAME/KEY: CDS
        (B) LOCATION: 26..292

(xi) SEQUENCE DESCRIPTION: SEQ ID NO: 3:

```
GGCCTGGCGG TGCTCCTGGA AAAGG ATG TTA GAC GCA GCC CTC CCA CCC TGC        52
                            Met Leu Asp Ala Ala Leu Pro Pro Cys
                            -18         -15                 -10

CCT ACT GTT GCG GCC ACA GCA GAT TGT GAA ATT TGC CCA GCC GTG AAG       100
Pro Thr Val Ala Ala Thr Ala Asp Cys Glu Ile Cys Pro Ala Val Lys
                -5              1               5

AGG GAT GTT GAC CTA TTC CTG ACG GGA ACC CCC GAC GAA TAT GTT GAG       148
Arg Asp Val Asp Leu Phe Leu Thr Gly Thr Pro Asp Glu Tyr Val Glu
        10              15              20

CAA GTG GCA CAA TAC AAA GCA CTA CCT GTA GTA TTG GAA AAT GCC AGA       196
Gln Val Ala Gln Tyr Lys Ala Leu Pro Val Val Leu Glu Asn Ala Arg
25              30              35

ATA CTG AAG AAC TGC GTT GAT GCA AAA ATG ACA GAA GAG GAT AAG GAG       244
Ile Leu Lys Asn Cys Val Asp Ala Lys Met Thr Glu Glu Asp Lys Glu
40              45              50              55

AAT GCT CTC AGC TTG CTG GAC AAA ATA TAC ACA AGT CCT CTG TGT TAA       292
Asn Ala Leu Ser Leu Leu Asp Lys Ile Tyr Thr Ser Pro Leu Cys
                60              65              70

AGGAGCCATC ACTGCCAGGA GCCCTAAGGA AGCCACTGAA CTGATCACTA AGTAGTCTCA     352

GCAGCCTGCC ATGTCCAGGT GTCTTACTAG AGGATTCCAG CAATAAAAGC CTTGCAATTC     412

AAACAAAAAA AAAAAA                                                     428
```

(2) INFORMATION FOR SEQ ID NO: 4:

(i) SEQUENCE CHARACTERISTICS:
        (A) LENGTH: 88 amino acids
        (B) TYPE: amino acid
        (D) TOPOLOGY: linear (ii) MOLECULE TYPE: protein (xi) SEQUENCE DESCRIPTION: SEQ ID NO: 4:

Met Leu Asp Ala Ala Leu Pro Pro Cys Pro Thr Val Ala Ala Thr Ala

```
            -18          -15                -10              -5
        Asp Cys Glu Ile Cys Pro Ala Val Lys Arg Asp Val Asp Leu Phe Leu
                     1              5                  10

Thr Gly Thr Pro Asp Glu Tyr Val Glu Gln Val Ala Gln Tyr Lys Ala
        15               20                  25                  30

Leu Pro Val Val Leu Glu Asn Ala Arg Ile Leu Lys Asn Cys Val Asp
                         35                  40                  45

Ala Lys Met Thr Glu Glu Asp Lys Glu Asn Ala Leu Ser Leu Leu Asp
                        50                  55                  60

Lys Ile Tyr Thr Ser Pro Leu Cys
                        65              70

(2) INFORMATION FOR SEQ ID NO: 5:

(i) SEQUENCE CHARACTERISTICS:
        (A) LENGTH: 485 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 8..337

(ix) FEATURE:
        (A) NAME/KEY: mat_peptide
        (B) LOCATION: 59..337

(xi) SEQUENCE DESCRIPTION: SEQ ID NO: 5:

TGACACG ATG AGG GGG GCA CTG CTT GTG CTG GCA TTG CTG GTG ACC CAA          49
        Met Arg Gly Ala Leu Leu Val Leu Ala Leu Leu Val Thr Gln
        -17         -15                 -10                 -5

GCG CTG GGC GTC AAG ATG GCG GAA ACT TGC CCC ATT TTT TAT GAC GTC          97
Ala Leu Gly Val Lys Met Ala Glu Thr Cys Pro Ile Phe Tyr Asp Val
              1               5                  10

TTT TTT GCG GTG GCC AAT GGA AAT GAA TTA CTG TTG GAC TTG TCC CTC         145
Phe Phe Ala Val Ala Asn Gly Asn Glu Leu Leu Leu Asp Leu Ser Leu
        15                  20                  25

ACA AAA GTC AAT GCT ACT GAA CCA GAG AGA ACA GCC ATG AAA AAA ATC         193
Thr Lys Val Asn Ala Thr Glu Pro Glu Arg Thr Ala Met Lys Lys Ile
30                  35                  40                  45

CAG GAT TGC TAC GTG GAG AAC GGA CTC ATA TCC AGG GTC TTG GAT GGA         241
Gln Asp Cys Tyr Val Glu Asn Gly Leu Ile Ser Arg Val Leu Asp Gly
                50                  55                  60

CTA GTC ATG ACA ACC ATC AGC TCC AGC AAA GAT TGC ATG GGT GAA GCA         289
Leu Val Met Thr Thr Ile Ser Ser Ser Lys Asp Cys Met Gly Glu Ala
                    65                  70                  75

GTT CAG AAC ACC GTA GAA GAT CTC AAG CTG AAC ACT TTG GGG AGA TGA         337
Val Gln Asn Thr Val Glu Asp Leu Lys Leu Asn Thr Leu Gly Arg
                80                  85                  90

ATTTTGCCAC TGATGCCCCT TCTGAGCCCC ATCCTCCTGC CCTGTTCTTT ACACCTAAAG       397

CTGGAATCCA GACACCTGTC CTCACCTAAT TCACTCTCAA TCAGGCTGAC TAGAATAAAA       457

TAACTGCATC TTAAAAAAAA AAAAAAA                                           485

(2) INFORMATION FOR SEQ ID NO: 6:

(i) SEQUENCE CHARACTERISTICS:
        (A) LENGTH: 109 amino acids
        (B) TYPE: amino acid
        (D) TOPOLOGY: linear
```

(ii) MOLECULE TYPE: protein (xi) SEQUENCE DESCRIPTION: SEQ ID NO: 6:

Met Arg Gly Ala Leu Leu Val Leu Ala Leu Leu Val Thr Gln Ala Leu
-17     -15                 -10                 -5

Gly Val Lys Met Ala Glu Thr Cys Pro Ile Phe Tyr Asp Val Phe Phe
    1           5                   10                  15

Ala Val Ala Asn Gly Asn Glu Leu Leu Asp Leu Ser Leu Thr Lys
                20              25              30

Val Asn Ala Thr Glu Pro Glu Arg Thr Ala Met Lys Lys Ile Gln Asp
            35              40              45

Cys Tyr Val Glu Asn Gly Leu Ile Ser Arg Val Leu Asp Gly Leu Val
            50              55              60

Met Thr Thr Ile Ser Ser Ser Lys Asp Cys Met Gly Glu Ala Val Gln
    65              70              75

Asn Thr Val Glu Asp Leu Lys Leu Asn Thr Leu Gly Arg
80              85              90

(2) INFORMATION FOR SEQ ID NO: 7:

(i) SEQUENCE CHARACTERISTICS:
        (A) LENGTH: 27 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 7:

Lys Arg Asp Val Asp Leu Phe Leu Thr Gly Thr Pro Asp Glu Tyr Va
1               5               10                  15

Glu Gln Val Ala Gln Tyr Lys Ala Leu Pro Val
            20              25

(2) INFORMATION FOR SEQ ID NO: 8:

(i) SEQUENCE CHARACTERISTICS:
        (A) LENGTH: 27 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 8:

Lys Ala Leu Pro Val Val Leu Glu Asn Ala Arg Ile Leu Lys Asn Cy
1               5               10                  15

Val Asp Ala Lys Met Thr Glu Glu Asp Lys Glu
            20              25

(2) INFORMATION FOR SEQ ID NO: 9:

(i) SEQUENCE CHARACTERISTICS:
        (A) LENGTH: 26 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 9:

```
Phe Phe Ala Val Ala Asn Gly Asn Glu Leu Leu Leu Asp Leu Ser Le
1               5                   10                  15

Thr Lys Val Asn Ala Thr Glu Pro Glu Arg
            20                  25
```

(2) INFORMATION FOR SEQ ID NO: 10:

(i) SEQUENCE CHARACTERISTICS:
        (A) LENGTH: 19 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 10:

```
Glu Glu Asp Lys Glu Asn Ala Leu Ser Leu Leu Asp Lys Ile Tyr Th
1               5                   10                  15

Ser Pro Leu
```

(2) INFORMATION FOR SEQ ID NO: 11:

(i) SEQUENCE CHARACTERISTICS:
        (A) LENGTH: 19 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 11:

```
Met Gly Glu Ala Val Gln Asn Thr Val Glu Asp Leu Lys Leu Asn Th
1               5                   10                  15

Leu Gly Arg
```

(2) INFORMATION FOR SEQ ID NO: 12:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 10..27

(xi) SEQUENCE DESCRIPTION: SEQ ID NO: 12:

```
GGGGGATCC AAA GCT CTG CCG GTT GTT                           27
          Lys Ala Leu Pro Val Val
          1               5
```

(2) INFORMATION FOR SEQ ID NO: 13:

(i) SEQUENCE CHARACTERISTICS:
        (A) LENGTH: 6 amino acids
        (B) TYPE: amino acid
        (D) TOPOLOGY: linear (ii) MOLECULE TYPE: protein (xi) SEQUENCE DESCRIPTION: SEQ ID NO: 13:

Lys Ala Leu Pro Val Val (2) INFORMATION FOR SEQ ID NO: 14:

(i) SEQUENCE CHARACTERISTICS:
        (A) LENGTH: 90 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 10..90

(xi) SEQUENCE DESCRIPTION: SEQ ID NO: 14:

```
GGGGGATCC AAA GCT CTG CCG GTT GTT CTG GAA AAC GCT CGT ATC CTG        48
          Lys Ala Leu Pro Val Val Leu Glu Asn Ala Arg Ile Leu
            1               5                  10

AAA AAC TGC GTT GAC GCT AAA ATG ACC GAA GAA GAC AAA GAA              90
Lys Asn Cys Val Asp Ala Lys Met Thr Glu Glu Asp Lys Glu
 15                  20                  25
```

(2) INFORMATION FOR SEQ ID NO: 15:

(i) SEQUENCE CHARACTERISTICS:
        (A) LENGTH: 27 amino acids
        (B) TYPE: amino acid
        (D) TOPOLOGY: linear (ii) MOLECULE TYPE: protein (xi) SEQUENCE DESCRIPTION: SEQ ID NO: 15:

```
Lys Ala Leu Pro Val Val Leu Glu Asn Ala Arg Ile Leu Lys Asn Cys
 1               5                  10                  15

Val Asp Ala Lys Met Thr Glu Glu Asp Lys Glu
                 20                  25
```

(2) INFORMATION FOR SEQ ID NO: 16:

(i) SEQUENCE CHARACTERISTICS:
        (A) LENGTH: 63 base pairs
        (B) TYPE: nucleic acid
        (C) STRANDEDNESS: single
        (D) TOPOLOGY: linear (ii) MOLECULE TYPE: cDNA (iv) ANTI-SENSE: YES (xi) SEQUENCE DESCRIPTION: SEQ ID NO: 16:

```
CAGAGACAGG TCCAGCAGCA GTTCGTTACC GTTAGCAACA GCGAAGAATT CTTTGTCTTC    60

TTC                                                                  63
```

(2) INFORMATION FOR SEQ ID NO: 17:

(i) SEQUENCE CHARACTERISTICS:
        (A) LENGTH: 21 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 17:

Glu Glu Asp Lys Glu Phe Phe Ala Val Ala Asn Gly Asn Glu Leu Le

```
                1               5                   10                  15
Leu Asp Leu Ser Leu
                20

(2) INFORMATION FOR SEQ ID NO: 18:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..45

(xi) SEQUENCE DESCRIPTION: SEQ ID NO: 18:

CTG GAC CTG TCT CTG ACC AAA GTT AAC GCT ACC GAA CCG GAA CGT       45
Leu Asp Leu Ser Leu Thr Lys Val Asn Ala Thr Glu Pro Glu Arg
1               5                   10                  15

(2) INFORMATION FOR SEQ ID NO: 19:

(i) SEQUENCE CHARACTERISTICS:
        (A) LENGTH: 15 amino acids
        (B) TYPE: amino acid
        (D) TOPOLOGY: linear (ii) MOLECULE TYPE: protein (xi) SEQUENCE DESCRIPTION: SEQ ID NO: 19:

Leu Asp Leu Ser Leu Thr Lys Val Asn Ala Thr Glu Pro Glu Arg
1               5                   10                  15

(2) INFORMATION FOR SEQ ID NO: 20:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (ii) MOLECULE TYPE: cDNA (iv) ANTI-SENSE: YES (xi) SEQUENCE DESCRIPTION: SEQ ID NO: 20:

GTCCGGGGTA CCGGTCAGGA ACAGGTCAAC GTCACGTTTA CGTTCCGGTT CGGT       54

(2) INFORMATION FOR SEQ ID NO: 21:

(i) SEQUENCE CHARACTERISTICS:
        (A) LENGTH: 18 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 21:

Thr Glu Pro Glu Arg Lys Arg Asp Val Asp Leu Phe Leu Thr Gly Th
1               5                   10                  15
Pro Asp (2) INFORMATION FOR SEQ ID NO: 22:
```

```
    (i) SEQUENCE CHARACTERISTICS:
        (A) LENGTH: 89 base pairs
        (B) TYPE: nucleic acid
        (C) STRANDEDNESS: single
        (D) TOPOLOGY: linear (ii) MOLECULE TYPE: peptide (ix) FEATURE:
        (A) NAME/KEY: CDS
        (B) LOCATION: 1..57

(xi) SEQUENCE DESCRIPTION: SEQ ID NO: 22:

ACC GGT ACC CCG GAC GAA TAC GTT GAA CAG GTT GCT CAG TAC AAA GCT        48
Thr Gly Thr Pro Asp Glu Tyr Val Glu Gln Val Ala Gln Tyr Lys Ala
1               5                   10                  15

CTG CCG GTT TAGTAGTCTA GACTGCAGAA GCTTGGATCC CC                        89
Leu Pro Val (2) INFORMATION FOR SEQ ID NO: 23:

(i) SEQUENCE CHARACTERISTICS:
        (A) LENGTH: 19 amino acids
        (B) TYPE: amino acid
        (D) TOPOLOGY: linear (ii) MOLECULE TYPE: protein (xi) SEQUENCE DESCRIPTION: SEQ ID NO: 23:

Thr Gly Thr Pro Asp Glu Tyr Val Glu Gln Val Ala Gln Tyr Lys Ala
1               5                   10                  15

Leu Pro Val (2) INFORMATION FOR SEQ ID NO: 24:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (ii) MOLECULE TYPE: cDNA (iv) ANTI-SENSE: YES (xi) SEQUENCE DESCRIPTION: SEQ ID NO: 24:

GGGGATCCAA GCTTCTGCAG TCTAGACTAC TAAACCGGCA GAGC                       44

(2) INFORMATION FOR SEQ ID NO: 25:

(i) SEQUENCE CHARACTERISTICS:
        (A) LENGTH: 4 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 25:

Ala Leu Pro Val
1

(2) INFORMATION FOR SEQ ID NO: 26:

(i) SEQUENCE CHARACTERISTICS:
        (A) LENGTH: 41 base pairs
        (B) TYPE: nucleic acid
```

(C) STRANDEDNESS: single
        (D) TOPOLOGY: linear (ii) MOLECULE TYPE: cDNA (ix) FEATURE:
        (A) NAME/KEY: CDS
        (B) LOCATION: 9..41

(xi) SEQUENCE DESCRIPTION: SEQ ID NO: 26:

GGGGATCC GAA GAA GAC AAA GAA AAC GCT CTG TCT CTG CTG          41
         Glu Glu Asp Lys Glu Asn Ala Leu Ser Leu Leu
         1               5                  10

(2) INFORMATION FOR SEQ ID NO: 27:

(i) SEQUENCE CHARACTERISTICS:
        (A) LENGTH: 11 amino acids
        (B) TYPE: amino acid
        (D) TOPOLOGY: linear (ii) MOLECULE TYPE: protein (xi) SEQUENCE DESCRIPTION: SEQ ID NO: 27:

Glu Glu Asp Lys Glu Asn Ala Leu Ser Leu Leu
1               5                  10

(2) INFORMATION FOR SEQ ID NO: 28:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (ii) MOLECULE TYPE: cDNA (iv) ANTI-SENSE: YES (xi) SEQUENCE DESCRIPTION: SEQ ID NO: 28:

TTCCAGAACA ACCGGCAGAG CTTTCAGCGG AGAGGTGTAG ATTTTGTCCA GCAGAGACAG          60

(2) INFORMATION FOR SEQ ID NO: 29:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 29:

Leu Ser Leu Leu Asp Lys Ile Tyr Thr Ser Pro Leu Lys Ala Leu Pr
1               5                  10                  15
Val Val Leu Glu
            20

(2) INFORMATION FOR SEQ ID NO: 30:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (ii) MOLECULE TYPE: cDNA (iv) ANTI-SENSE: YES (xi) SEQUENCE DESCRIPTION: SEQ ID NO: 30:

TTCAACGGTG TTCTGAACAG CTTCACCCAT AACCGGCAGA GCTTTGTACT GAGC        54

(2) INFORMATION FOR SEQ ID NO: 31:

(i) SEQUENCE CHARACTERISTICS:
        (A) LENGTH: 18 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 31:

Ala Gln Tyr Lys Ala Leu Pro Val Met Gly Glu Ala Val Gln Asn Th
1               5                   10                  15

Val Glu (2) INFORMATION FOR SEQ ID NO: 32:

(i) SEQUENCE CHARACTERISTICS:
        (A) LENGTH: 65 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..45

(xi) SEQUENCE DESCRIPTION: SEQ ID NO: 32:

CAG AAC ACC GTT GAA GAC CTG AAA CTG AAC ACC CTG GGT CGT TGAATGTAAC    52
Gln Asn Thr Val Glu Asp Leu Lys Leu Asn Thr Leu Gly Arg
1               5                   10                  15

TGCAGAATTC CCC                                                       65

(2) INFORMATION FOR SEQ ID NO: 33:

(i) SEQUENCE CHARACTERISTICS:
        (A) LENGTH: 14 amino acids
        (B) TYPE: amino acid
        (D) TOPOLOGY: linear (ii) MOLECULE TYPE: protein (xi) SEQUENCE DESCRIPTION: SEQ ID NO: 33:

Gln Asn Thr Val Glu Asp Leu Lys Leu Asn Thr Leu Gly Arg
1               5                   10

(2) INFORMATION FOR SEQ ID NO: 34:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 9..20

(xi) SEQUENCE DESCRIPTION: SEQ ID NO: 34:

```
GGGGATCC GAA GAA GAC AAA                                                20
         Glu Glu Asp Lys
         1
```

(2) INFORMATION FOR SEQ ID NO: 35:

(i) SEQUENCE CHARACTERISTICS:
        (A) LENGTH: 4 amino acids
        (B) TYPE: amino acid
        (D) TOPOLOGY: linear (ii) MOLECULE TYPE: protein (xi) SEQUENCE DESCRIPTION: SEQ ID NO: 35:

```
Glu Glu Asp Lys
1
```

(2) INFORMATION FOR SEQ ID NO: 36:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: cDNA (iv) ANTI-SENSE: YES (xi) SEQUENCE DESCRIPTION: SEQ ID NO: 36:

```
GGGGAATTCT GCAGTTACAT TCATCTCCCC AAAGT                                  35
```

(2) INFORMATION FOR SEQ ID NO: 37:

(i) SEQUENCE CHARACTERISTICS:
        (A) LENGTH: 4 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 37:

```
Thr Leu Gly Arg
1
```

(2) INFORMATION FOR SEQ ID NO: 38:

(i) SEQUENCE CHARACTERISTICS:
        (A) LENGTH: 288 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..288

(xi) SEQUENCE DESCRIPTION: SEQ ID NO: 38:

```
ATG GGT CAC CAC CAC CAC CAC CAC GAA TTC CTG GTT CCG CGT GGA TCC          48
Met Gly His His His His His His Glu Phe Leu Val Pro Arg Gly Ser
1               5                   10                  15

AAA GCT CTG CCG GTT GTT CTG GAA AAC GCT CGT ATC CTG AAA AAC TGC          96
Lys Ala Leu Pro Val Val Leu Glu Asn Ala Arg Ile Leu Lys Asn Cys
                20                  25                  30

GTT GAC GCT AAA ATG ACC GAA GAA GAC AAA GAA TTC TTC GCT GTT GCT         144
```

```
Val Asp Ala Lys Met Thr Glu Glu Asp Lys Glu Phe Phe Ala Val Ala
         35                  40                  45

AAC GGT AAC GAA CTG CTG CTG GAC CTG TCT CTG ACC AAA GTT AAC GCT      192
Asn Gly Asn Glu Leu Leu Leu Asp Leu Ser Leu Thr Lys Val Asn Ala
 50                  55                  60

ACC GAA CCG GAA CGT AAA CGT GAC GTT GAC CTG TTC CTG ACC GGT ACC      240
Thr Glu Pro Glu Arg Lys Arg Asp Val Asp Leu Phe Leu Thr Gly Thr
 65                  70                  75                  80

CCG GAC GAA TAC GTT GAA CAG GTT GCT CAG TAC AAA GCT CTG CCG GTT      288
Pro Asp Glu Tyr Val Glu Gln Val Ala Gln Tyr Lys Ala Leu Pro Val
                 85                  90                  95
```

(2) INFORMATION FOR SEQ ID NO: 39:

(i) SEQUENCE CHARACTERISTICS:
        (A) LENGTH: 96 amino acids
        (B) TYPE: amino acid
        (D) TOPOLOGY: linear (ii) MOLECULE TYPE: protein (xi) SEQUENCE DESCRIPTION: SEQ ID NO: 39:

```
Met Gly His His His His His His Glu Phe Leu Val Pro Arg Gly Ser
 1               5                  10                  15

Lys Ala Leu Pro Val Val Leu Glu Asn Ala Arg Ile Leu Lys Asn Cys
         20                  25                  30

Val Asp Ala Lys Met Thr Glu Glu Asp Lys Glu Phe Phe Ala Val Ala
         35                  40                  45

Asn Gly Asn Glu Leu Leu Leu Asp Leu Ser Leu Thr Lys Val Asn Ala
 50                  55                  60

Thr Glu Pro Glu Arg Lys Arg Asp Val Asp Leu Phe Leu Thr Gly Thr
 65                  70                  75                  80

Pro Asp Glu Tyr Val Glu Gln Val Ala Gln Tyr Lys Ala Leu Pro Val
                 85                  90                  95
```

(2) INFORMATION FOR SEQ ID NO: 40:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 40:

GGGGAATTCA AGAGGGATGT TGACCTA                                      27

(2) INFORMATION FOR SEQ ID NO: 41:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 41:

```
Lys Arg Asp Val Asp Leu
 1               5
```

(2) INFORMATION FOR SEQ ID NO: 42:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 42:

CTACCTGTAT TTTTTGCGGT GGCCAAT                                                   27

(2) INFORMATION FOR SEQ ID NO: 43:

(i) SEQUENCE CHARACTERISTICS:
            (A) LENGTH: 9 amino acids
            (B) TYPE: amino acid
            (D) TOPOLOGY: linear (ii) MOLECULE TYPE: peptide (v) FRAGMENT TYPE: internal (xi) SEQUENCE DESCRIPTION: SEQ ID NO: 43:

Leu Pro Val Phe Phe Ala Val Ala Asn
1               5

(2) INFORMATION FOR SEQ ID NO: 44:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 44:

CCAGAGAGAA AAGCACTACC TGTAGTA                                                   27

(2) INFORMATION FOR SEQ ID NO: 45:

(i) SEQUENCE CHARACTERISTICS:
            (A) LENGTH: 9 amino acids
            (B) TYPE: amino acid
            (D) TOPOLOGY: linear (ii) MOLECULE TYPE: peptide (v) FRAGMENT TYPE: internal (xi) SEQUENCE DESCRIPTION: SEQ ID NO: 45:

Pro Glu Arg Lys Ala Leu Pro Val Val
1               5

(2) INFORMATION FOR SEQ ID NO: 46:

(i) SEQUENCE CHARACTERISTICS:
            (A) LENGTH: 36 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 46:

ATTGGCCACC GCAAAAAATA CAGGTAGTGC TTTGTA                                          36

(2) INFORMATION FOR SEQ ID NO: 47:

(i) SEQUENCE CHARACTERISTICS:
           (A) LENGTH: 12 amino acids
           (B) TYPE: amino acid
           (D) TOPOLOGY: linear (ii) MOLECULE TYPE: peptide (v) FRAGMENT TYPE: internal (xi) SEQUENCE DESCRIPTION: SEQ ID NO: 47:

Asn Ala Val Ala Phe Phe Val Pro Leu Ala Lys Tyr
1               5                   10

(2) INFORMATION FOR SEQ ID NO: 48:

(i) SEQUENCE CHARACTERISTICS:
           (A) LENGTH: 27 base pairs
           (B) TYPE: nucleic acid
           (C) STRANDEDNESS: single
           (D) TOPOLOGY: linear (ii) MOLECULE TYPE: cDNA (xi) SEQUENCE DESCRIPTION: SEQ ID NO: 48:

TAGTGCTTTT CTCTCTGGTT CAGTAGC                                    27

(2) INFORMATION FOR SEQ ID NO: 49:

(i) SEQUENCE CHARACTERISTICS:
           (A) LENGTH: 9 amino acids
           (B) TYPE: amino acid
           (D) TOPOLOGY: linear (ii) MOLECULE TYPE: peptide (v) FRAGMENT TYPE: internal (xi) SEQUENCE DESCRIPTION: SEQ ID NO: 49:

Leu Ala Lys Arg Glu Pro Glu Thr Ala
1               5

(2) INFORMATION FOR SEQ ID NO: 50:

(i) SEQUENCE CHARACTERISTICS:
           (A) LENGTH: 29 base pairs
           (B) TYPE: nucleic acid
           (C) STRANDEDNESS: single
           (D) TOPOLOGY: linear (ii) MOLECULE TYPE: cDNA (xi) SEQUENCE DESCRIPTION: SEQ ID NO: 50:

GGGGATCCTT ACTCCTTATC CTCTTCTGT                                  29

(2) INFORMATION FOR SEQ ID NO: 51:

(i) SEQUENCE CHARACTERISTICS:
           (A) LENGTH: 6 amino acids
           (B) TYPE: amino acid
           (D) TOPOLOGY: linear (ii) MOLECULE TYPE: peptide (v) FRAGMENT TYPE: internal (xi) SEQUENCE DESCRIPTION: SEQ ID NO: 51:

Glu Lys Asp Glu Glu Thr
1               5

(2) INFORMATION FOR SEQ ID NO: 52:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 52:

GGGGAATTCA AAGCACTACC TGTAGTA                                              27

(2) INFORMATION FOR SEQ ID NO: 53:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 53:

Lys Ala Leu Pro Val Val
1            5

(2) INFORMATION FOR SEQ ID NO: 54:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 54:

GATAAGGAGA AGAGGGATGT TGACCTA                                              27

(2) INFORMATION FOR SEQ ID NO: 55:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 55:

Asp Lys Glu Lys Arg Asp Val Asp Leu
1            5

(2) INFORMATION FOR SEQ ID NO: 56:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 56:

CTACCTGTAT TTTTTGCGGT GGCCAAT                                              27

(2) INFORMATION FOR SEQ ID NO: 57:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 57:

Leu Pro Val Phe Phe Ala Val Ala Asn
1               5

(2) INFORMATION FOR SEQ ID NO: 58:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 58:

TAGGTCAACA TCCCTCTTCT CCTTATCCTC TTCTGT                    36

(2) INFORMATION FOR SEQ ID NO: 59:

(i) SEQUENCE CHARACTERISTICS:
        (A) LENGTH: 12 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 59:

Leu Asp Val Asp Arg Lys Glu Lys Asp Glu Glu Thr
1               5                   10

(2) INFORMATION FOR SEQ ID NO: 60:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 60:

CGCAAAAAAT ACAGGTAGTG CTTTGTA                              27

(2) INFORMATION FOR SEQ ID NO: 61:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 61:

Ala Phe Phe Val Pro Leu Ala Lys Tyr (2) INFORMATION FOR SEQ ID NO: 62:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 62:

GGGGATCCTT ATCTCTCTGG TTCAGTAGC                     29

(2) INFORMATION FOR SEQ ID NO: 63:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 63:

Arg Glu Pro Glu Thr Ala
1          5

(2) INFORMATION FOR SEQ ID NO: 64:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 64:

GGGGAATTCT TGCGGTGGC CAATGGA                       27

(2) INFORMATION FOR SEQ ID NO: 65:

(i) SEQUENCE CHARACTERISTICS:
        (A) LENGTH: 7 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 65:

Phe Phe Ala Val Ala Asn Gly
1          5

(2) INFORMATION FOR SEQ ID NO: 66:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 66:

AAGAGGGATG TTGACCTATT C                                          21

(2) INFORMATION FOR SEQ ID NO: 67:

(i) SEQUENCE CHARACTERISTICS:
        (A) LENGTH: 7 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 67:

Lys Arg Asp Val Asp Leu Pro
1               5

(2) INFORMATION FOR SEQ ID NO: 68:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 68:

TAGGTCAACA TCCCTCTTTC TCTCTGGTTC AGTAGCATT                        39

(2) INFORMATION FOR SEQ ID NO: 69:

(i) SEQUENCE CHARACTERISTICS:
        (A) LENGTH: 13 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 69:

Leu Asp Val Asp Arg Lys Arg Glu Pro Glu Thr Ala Asn
1               5                   10

(2) INFORMATION FOR SEQ ID NO: 70:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 70:

GGGGATCCTC ACTCCTTATC CTCTTCTGTC AT                              32

(2) INFORMATION FOR SEQ ID NO: 71:

(i) SEQUENCE CHARACTERISTICS:
        (A) LENGTH: 7 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 71:

```
Glu Lys Asp Glu Glu Thr Met
1               5
```

(2) INFORMATION FOR SEQ ID NO: 72:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 72:

```
Leu Val Pro Arg Gly Ser
1               5
```

(2) INFORMATION FOR SEQ ID NO: 73:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 73:

```
Met Gly His His His His His His Glu Phe
1               5                   10
```

(2) INFORMATION FOR SEQ ID NO: 74:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 74:

```
Gly Ala Ala Thr Thr Cys
1               5
```

(2) INFORMATION FOR SEQ ID NO: 75:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 75:

```
Gly Gly Ala Thr Cys Cys
1               5
```

(2) INFORMATION FOR SEQ ID NO: 76:

(i) SEQUENCE CHARACTERISTICS:
        (A) LENGTH: 14 amino acids
        (B) TYPE: amino acid
        (D) TOPOLOGY: linear

```
    (ii) MOLECULE TYPE: peptide (v) FRAGMENT TYPE: internal (xi) SEQUENCE DESCRIPTION: SEQ ID NO: 76:

Met Gly His His His His His Leu Val Pro Arg Gly Ser
1               5                   10
```

RECOMBITOPE PEPTIDES

RELATED APPLICATIONS

This application is a continuation of application Ser. No. 08/464,363 filed Jun. 5, 1995 now abandoned entitled "RECOMBINANT PEPTIDES COMPRISING T CELL EPITOPES OF THE CAT ALLERGEN, FEL D I", which is a continuation of U.S. application Ser. No. 07/807,529 filed Dec. 13, 1991, now U.S. Pat. No. 5,547,669, issued Aug. 20, 1996 entitled "RECOMBINANT PEPTIDES COMPRISING T CELL EPITOPES OF THE CAT ALLERGEN, FEL D I", which is a continuation-in-part of U.S. Ser. No. 07/662,276 entitled "A HUMAN T CELL REACTIVE CAT PROTEIN ISOLATED FROM HOUSE DUST AND USES THEREFOR," filed Feb. 28, 1991 (abandoned), which is a continuation-in-part of U.S. Ser. No. 07/431,565 entitled "A HUMAN T CELL REACTIVE CAT PROTEIN ISOLATED FROM HOUSE DUST AND USES THEREFOR," filed Nov. 3, 1989 (abandoned), the teachings of which are incorporated herein by reference.

BACKGROUND OF THE INVENTION

T lymphocytes can mediate and regulate both the specific and non-specific effector mechanisms of immune responses. CD4+ T lymphocytes provide help for antibody production and secrete cytokines which modulate the growth of other T cells and the growth and differentiation of other immune cells such as monocytes and granulocytes. Functional and biochemical studies have demonstrated that the generation of cellular immune responses depends upon antigen receptors on T cells that recognize peptide fragments of foreign proteins associated with products of the major histocompatibility complex (MHC) that are expressed on antigen-presenting accessory cells. Recent advances in technology have made it possible to culture efficiently antigen-specific human and mouse T cell lines and clones in vitro. In addition, it is now possible to produce large amounts of protein antigens or their fragments using recombinant DNA technology or solid phase peptide synthesis. Thus, in the last few years, several research groups have begun to determine the linear amino acid sequences of antigenic proteins that are recognized by T cells in association with MHC (T cell epitopes).

Peptides derived from a variety of protein antigens, including bacterial and viral pathogens, autoantigens, allergens and other experimental antigens such as hen egg lysozyme (HEL), ovalbumin (OVA) and lambda repressor (cl) have been examined for the ability to stimulate antigen-specific T cells. A wide size spectrum of peptides has been reported to serve as T cell epitopes. For example, OVA amino acid residues 324–339 (Shimonkevitz, R. et al., *J. Immunol.*, 133:2167 (1984)), HEL amino acid residues 74–96 (Shastri, N. et al., *J. Exp. Med.* 164:882–896 (1986); and lambda repressor (cl) amino acid residues 12–26 (Lai, M.-Z et al., *J. Immunol.*, 139:3973–3980 (1987)) have been demonstrated to trigger efficiently whole protein-primed T cells. A peptide derived from Hepatitis B surface antigen (HBsAg amino acid residues 19–33) has recently been shown to stimulate T cell responses in a majority of human subjects who had been immunized with a recombinant hepatitis B vaccine (Schad, V. C. et al., *Seminars in Immunol.*, 3:217–224 (1991)). A major mycobacterial antigen 65-kD protein has also been epitope-mapped (Lamb, J. R. et al., *EMBO J.*, 6(5):1245–1249 (1987)). T cell epitopes have been identified in the peptides comprised of amino acid residues 112–132 and 437–459 of the 65-kD protein. Myelin basic protein (MBP), an autoantigen which induces experimental autoimmune encephalomyelitis (EAE) and the presumed autoantigen in multiple sclerosis (MS) has also been epitope-mapped in both human (Ota, K. et al., *Nature*, 346:183–187 (1990)) and rodent (Zamvil et al., *Nature* 324:258–260(1986)) systems. Ota et al. have identified a major T cell epitope recognized by MS patients, MBP amino acid residues 84–102. Minor epitopes (MBP amino acid residues 143–168, 61–82, 124–42 and 31–50) recognized by T cells from MS patients were also described. Zamvil et al. have shown that MBP amino acid residues 1–11 contain the major T cell epitope(s) causing EAE, in susceptible rodent strains.

T cell epitopes present in allergenic proteins have very recently been described (O'Hehir, R. et al., *Ann. Rev. Immunol.*, 9:67–95 (1991)). Several peptides derived from the house dust mite allergen Der p I have been shown to be T cell-reactive (Thomas, W. R., et al. In *Epitopes of Atopic Allergens Proceedings of Workshop from XIV Congress of the European Academy of Allergy and Clinical Immunology*, Berlin (September 1989) pp. 77–82; O'Hehir, R. E. *Annual Review Immunology* 9:67–95 (1991); Stewart, G. A. et al In: *Epitopes of Atopic Allergens Proceedings of Workshop from XIV Congress of the European Academy of Allergy and Clinical Immunology*, Berlin (September 1989) pp 41–47; and Yessel, H. et al. In: *T Cell Activation in Health and Disease: Discrimination Between Immunity and Tolerance*, Conference 22–26 (September 1990) Trinity College, Oxford U.K.). A T cell-stimulatory peptide derived from the short ragweed allergen Amb a I amino acid residues 54–65 has also been reported (Rothbard, J. B. et al., *Cell*, 52: 515–523 (1988). Using a panel of T cell clones derived from a rye grass-allergic individual, Perez et al. demonstrated that T cell epitopes are contained within amino acid residues 191–210 of the protein allergen Lol p I (Perez, M. et al., *J. Biol. Chem.*, 265(27):16210–16215 (1990)).

SUMMARY OF THE INVENTION

The present invention provides isolated peptides having T cell stimulating activity, termed recombitope™ peptides. Recombitope peptides of the invention preferably have human T cell stimulating activity. In addition, recombitope peptides of the invention preferably comprise at least two T cell epitopes derived from the same or from different protein antigens, and more preferably comprise at least two regions, each region comprising at least one T cell epitope derived from a protein antigen and each region preferably having human T cell stimulating activity. In some instances, recombitope peptides comprise three such regions derived from the same or from different protein antigens. As used herein, a region of a recombitope peptide comprises at least 5 and preferably at least 7 amino acid residues. Typically, recombitope peptides comprise regions which are arranged in a configuration different from a naturally-occurring configuration of the regions in a protein antigen in order to eliminate undesired properties associated with the secondary or tertiary structure of the protein antigen while maintaining the primary structure dependent human T cell stimulating activity. For example, the regions can be derived from the same protein antigen and arranged in a noncontiguous configuration or in a noncontiguous configuration and a nonsequential order.

Recombitope peptides of the invention can be derived from protein allergens. These recombitope peptides preferably have minimal immunoglobulin E stimulating activity and bind immunoglobulin E to a substantially lesser extent than protein allergens from which the recombitope peptides are derived bind immunoglobulin E. More preferably, recombitope peptides derived from protein allergens do not bind immunoglobulin E specific for the protein allergens in a substantial percentage (at least about 75%) of the individuals sensitive to the protein allergens, or if such binding occurs, such binding does not result in mediator release, e.g. histamine, from mast cells or basophils. In addition, recombitope peptides can be derived from autoantigens, such as insulin, myelin basic protein and acetylcholine receptors. These recombitope peptides preferably do not bind immunoglobulin specific for the autoantigen in a substantial percentage (at least about 75%) of a population of individuals sensitive to the autoantigen. Further, recombitope peptides derived from protein allergens or other protein antigens can be designed such that an undesirable property of the native protein (e.g., enzymatic activity) can be eliminated for therapeutic purposes.

The invention also provides methods of diagnosing sensitivity to a protein allergen or other protein antigen in an individual, methods to treat such sensitivity and therapeutic compositions comprising one or more recombitope peptides. For example, methods of detecting specific Delayed Type Hypersensitivity and/or specific Immediate Type Hypersensitivity in an individual to at least one protein allergen or other protein antigen are disclosed. According to one method, a specific Delayed Type Hypersensitivity test utilizing a recombitope peptide of the invention can be administered to an individual, and the extent to which a specific Delayed Type Hypersensitivity reaction occurs in the individual can be determined. In another method, the presence of immunoglobulin E specific for at least one protein allergen can be determined in an individual and the ability of T cells of the individual to respond to T cell epitope(s) of the protein allergen assessed. In this embodiment, a specific Immediate Type Hypersensitivity test utilizing a protein allergen or a portion thereof, or a modified form of a protein allergen or a portion thereof, each of which binds immunoglobulin E specific for the protein allergen is administered to individuals. Additionally, a specific Delayed Type Hypersensitivity test utilizing a modified form of the protein allergen or a portion thereof, or a protein allergen produced recombinantly, or a recombitope peptide derived from a protein allergen, each of which has human T cell stimulating activity and each of which does not bind immunoglobulin E (IgE) specific for the protein allergen or if binding occurs, such binding does not result in release of mediators from mast cells or basophils in a substantial percentage of the population of individuals sensitive to the allergen (e.g., at least about 75%) is administered to the same individuals prior to, simultaneously with, or subsequent to administration of the Immediate Type Hypersensitivity test. Those individuals exhibiting both a specific Immediate Type Hypersensitivity reaction and a specific Delayed Type Hypersensitivity reaction are administered a therapeutically effective amount of a therapeutic composition comprising the modified form of the protein allergen or portion thereof, the recombinantly produced protein allergen, or the recombitope peptide derived from a protein allergen, and a pharmaceutically acceptable carrier or diluent, since it is believed that administering to an individual such a therapeutic composition will serve to desensitize the individual to the protein allergen.

Recombitope peptides derived from protein antigens and having human T cell stimulating activity can also be used in other methods of determining in individuals the presence of immunoglobulin specific for a protein antigen and the ability of T cells of the individuals to be stimulated by T cell epitope(s) of the protein antigen. One such method comprises combining a first blood sample obtained from an individual or at least one portion of the sample with the protein antigen, a modified form of the protein antigen, or a portion of either, each of which binds immunoglobulin specific for the protein antigen. The sample and antigen are combined under conditions appropriate for binding of blood components, e.g., immunoglobulin, in the sample or portion thereof with the protein antigen, modified protein antigen or portion of either of the antigens. If binding occurs, a second blood sample obtained from the individual or a second portion of the original sample is combined with a recombitope peptide comprising at least two regions derived from the protein antigen, a modified form of the protein antigen or a portion thereof, or the protein antigen produced recombinantly, each of which has human T cell stimulating activity and each of which preferably does not bind immunoglobulin specific for the protein antigen in a substantial percentage of the population of individuals sensitive to the antigen (e.g., at least about 75%), in order to determine whether T cell stimulation occurs. If T cell stimulation occurs, the individual is preferably administered a therapeutically effective amount of a therapeutic composition comprising the modified form of the protein antigen or a portion thereof, the recombinantly produced protein antigen, or the recombitope peptide, and a pharmaceutically acceptable carrier or diluent, since it is believed that administering to an individual such a therapeutic composition will desensitize the individual to the protein antigen.

Methods for designing recombitope peptides of the invention are also provided where the protein antigen to which the individual is sensitive has unknown or ill-defined T cell epitopes (e.g., some or all of the peptide regions of the protein antigen which have human T cell stimulating activity to the protein antigen have not been defined by standard T cell biology techniques, e.g., *Current Protocols in Immunology*, edited by Coligan, J. E. et al., volume 1, (1991), or the precise human T cell epitopes of the protein antigen have not been defined by fine mapping techniques). According to one method, the known protein structure of an allergen or other protein antigen is reviewed and the allergen or other antigen is theoretically divided into at least two peptide regions of desired lengths. By theoretically is meant something that does not actually take place but rather a thought process, e.g., occurs on paper or in one's head. This division can be arbitrary, can be made according to an algorithm, or can be wholly or partially based on regions of the protein antigen known to have T cell stimulating activity, preferably human T cell stimulating activity. When just a few regions of a protein antigen which have T cell stimulating activity are known or when all the regions of the protein antigen which have human T cell stimulating activity are unknown, preferably, at least 50% and more preferably, the entire protein is divided into peptide regions of desired lengths. The peptide regions are then theoretically arranged to form at least one recombitope peptide in which the regions are rearranged in a noncontiguous order. Subsequently, at least one recombitope peptide having a rearranged configuration is produced and the ability of the recombitope peptide to stimulate human T cells is determined. In a further embodiment, the ability of a recombitope peptide found to have human T cell stimulating activity is tested to determine its ability to bind immunoglobulin specific for the allergen or other antigen, or is tested for the absence of another undesired property (e.g., protease activity).

BRIEF DESCRIPTION OF THE DRAWINGS

FIG. 1 is the nucleic acid sequence and deduced amino acid sequence of chain 1 of the human T Cell Reactive Feline Protein (TRFP) including leader sequences A and B.

FIG. 2 is the nucleic acid sequence and deduced amino acid sequence of chain 2 of TRFP including a leader sequence.

FIG. 4 is the amino acid sequences of peptide X, peptide Y, peptide Z, peptide A and peptide B of TRFP, each of which contains at least one T cell epitope of TRFP.

FIG. 7 is the nucleic acid sequences of oligonucleotides C, D, E, F, G, H, and I used in the construction of the recombitope peptide YZX and oligonucleotides J, K, L, M, N and O used in the construction of the recombitope peptide AYZXB.

FIG. 8 is the nucleic acid sequence (utilizing *E. coli* expression codons) and the deduced amino acid sequence comprising recombitope peptide YZX. A thrombin cleavage site is shown.

FIG. 9 is a schematic representation of the construction of a recombitope peptide YZX using PCR techniques with cDNA isolated from TRFP as a template.

FIG. 10 is the nucleic acid sequences of primers used in the construction of recombitope peptides XZY, YXZ, and ZXY.

FIG. 12 is a schematic representation of the construction of a recombitope peptide derived from phospholipase $A_2$, which has ill-defined T cell epitopes.

DETAILED DESCRIPTION OF THE INVENTION

Figure 3:
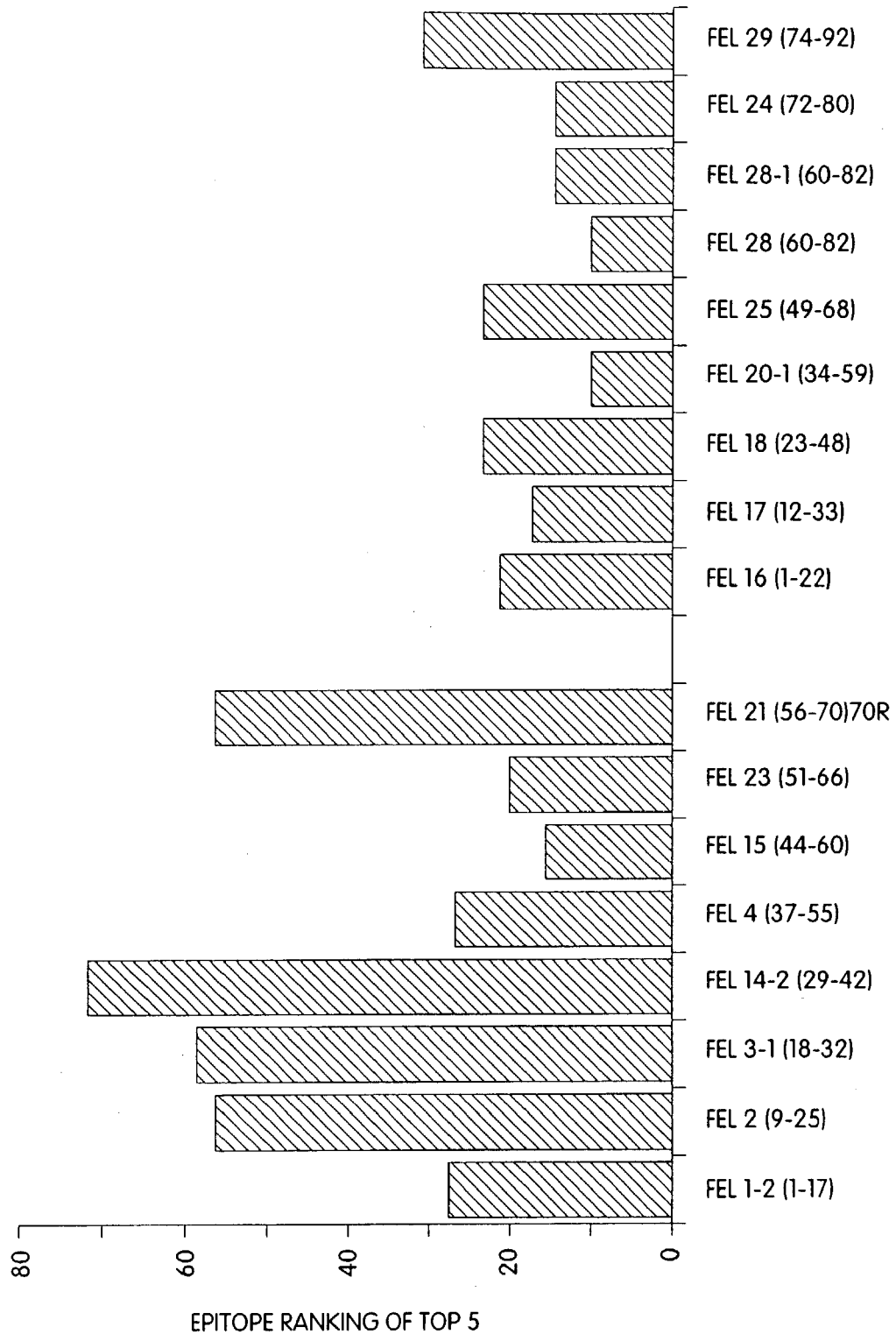
FIG. 3 is a graphic representation depicting the response of T cells isolated from cat-allergic patients and primed with affinity-purified TRFP to overlapping TRFP peptides analyzed by the ranked sum of peptide responses.
Figure 5:
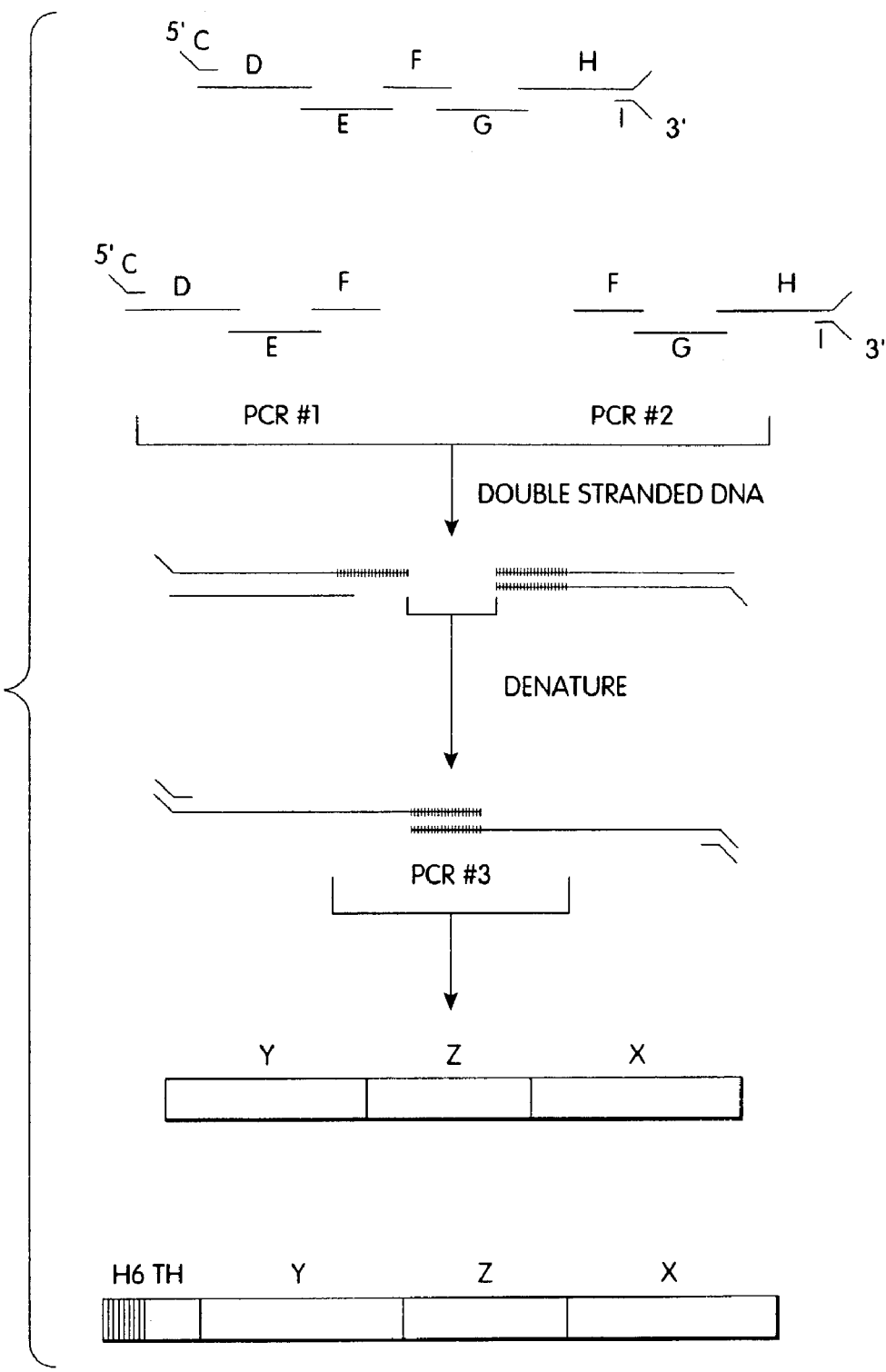
FIG. 5 is a schematic representation of the construction of a recombitope peptide YZX using polymerase chain reaction (PCR) techniques.

The present invention relates to isolated peptides, termed recombitope peptides, having T cell stimulating activity, such as induction of T cell proliferation, lymphokine secretion and/or T cell anergy/tolerization. Recombitope peptides of the invention preferably have human T cell stimulating activity and are useful in diagnosing and treating sensitivity in an individual to a protein allergen, autoantigen or other protein antigen. In general, preferred recombitope peptides within the scope of the invention comprise at least two regions derived from the same or from different protein allergens or other protein antigens, each region preferably having human T cell stimulating activity as determined by standard T cell biology techniques, and thus comprising at least one T cell epitope. In order to determine precise T cell epitopes by, for example, fine mapping techniques, the peptide regions comprising at least one T cell epitope that have been defined by standard T cell biology techniques can be modified by addition or deletion of amino acid residues at either the amino or carboxy terminus of the peptide regions and tested to determine a change in T cell reactivity to the modified peptide. Furthermore, if two or more peptide regions which share an area of overlap are found to have human T cell stimulating activity, as determined be standard T cell biology techniques, additional peptides can be produced comprising all or a portion of such peptide regions and these additional peptides can be tested by the above fine mapping procedure. As a result of fine mapping, a set of human T cell epitopes comprising amino acid residues essential to T cell recognition can be produced.

Recombitope peptides of the invention can be produced by recombinant DNA techniques in a host cell transformed with a nucleic acid sequence coding for such recombitope peptide, or by chemical synthesis, or in certain limited situations by chemical cleavage of a protein allergen or other protein antigen. When produced by recombinant techniques, host cells transformed with nucleic acid encoding a recombitope peptide are cultured in a medium suitable for the cells and recombitope peptides can be purified from cell culture medium, host cells, or both using techniques known in the art for purifying peptides or proteins including ion-exchange chromatography, isoelectricfocusing, gel filtration chromatography, ultrafiltration, electrophoresis or immunopurification with antibodies specific for the recombitope peptide, the protein allergen or other antigen from which the recombitope peptide is derived, or a portion thereof. Thus, one aspect of this invention provides a recombitope peptide produced in a host cell transformed with a nucleic acid sequence coding for a recombitope peptide, or the functional equivalent of the nucleic acid sequence. Recombitope peptides of the invention are isolated such that the recombitope peptide is substantially free of cellular material or culture medium when produced by recombinant DNA techniques, or substantially free of chemical precursors or other chemicals when synthesized chemically, or obtained by chemical cleavage of a protein allergen or other protein antigen.

To obtain preferred recombitope peptides of the present invention comprising at least two T cell epitopes of a protein allergen or other protein antigen or at least two regions, each region comprising at least one T cell epitope of a protein allergen or other antigen, the T cell epitopes or regions containing T cell epitope(s) are arranged in a configuration different from a naturally-occurring configuration of the T cell epitopes or regions in the allergen or antigen. For example, the T cell epitopes or regions containing T cell epitope(s) can be arranged in a noncontiguous configuration and can preferably be derived from the same protein allergen or other antigen. Noncontiguous is defined as an arrangement of amino acids comprising T cell epitopes or regions containing T cell epitope(s) which is different than that of an amino acid sequence present in the protein allergen or other protein antigen from which the epitopes or regions are derived. Furthermore, the noncontiguous T cell epitopes or regions containing T cell epitopes can be arranged in a nonsequential order (e.g., in an order different from the order of the amino acids of the native protein allergen or other protein antigen from which the T cell epitopes or region containing T cell epitope(s) are derived in which amino acids are arranged from an amino terminus to a carboxy terminus.) A preferred recombitope peptide comprises at least 15%, more preferably at least 30%, even more preferably at least 50% and most preferably up to 100% of the T cell epitopes of a protein allergen or other protein antigen.

In the situation where the T cell epitopes of a protein allergen or other protein antigen are unknown or ill-defined (e.g., some or all of the peptide regions of the protein antigen which have human T cell stimulating activity have not been defined by standard T cell biology techniques or the precise human T cell epitopes of the protein antigen have not been defined by fine mapping techniques), a recombitope peptide may be obtained by reviewing the known protein structure of an allergen or other antigen and theoretically dividing the allergen or antigen into at least two peptide regions of desired lengths. For example, the protein sequence of the allergen or other antigen can be systematically divided into at least two non-overlapping peptide regions of desired lengths, or at least two overlapping peptide regions of desired lengths and theoretically arranged to form at least one recombitope peptide in which the at least two regions are rearranged in a noncontiguous and preferably nonsequential order. This division into peptide regions can be arbitrary, can be made according to an algorithm, or can be wholly or partially based on regions of the protein antigen known to comprise at least one T cell epitope.

When just a few of the peptide regions of the protein allergen or other protein antigen comprising at least one T cell epitope are known or when all the regions of the protein allergen or other protein antigens which have human T cell stimulating activity are unknown, preferably, at least 50% of the entire protein sequence of the protein allergen or other protein antigen and more preferably, the entire protein sequence of the protein allergen or other protein antigen is divided and rearranged into one or more recombitope peptides. The purpose behind using such a large percentage of the protein sequence of the protein antigen in forming the recombitope peptide is so that the resultant recombitope peptide comprises at least 15%, more preferably at least 30%, even more preferably at least 50%, and most preferably at least 100% of the T cell epitopes of the protein antigen. Of course, it the few peptide regions of the protein antigen each known to comprise at least one T cell epitope constitute the above-stated percentage of the T cell epitopes of the protein antigen and such peptide regions do not constitute at least 50% of the entire protein sequence of the protein antigen, it is not necessary to use such a large percentage of the entire protein sequence in forming the recombitope peptide. According to this method, recombitope peptides can then be produced recombinantly or synthetically and the ability of the recombitope peptide to stimulate human T cells can be determined. When the recombitope peptide comprises regions derived from a protein allergen, the individual peptide regions can be produced and tested to determine which regions bind immunoglobulin E specific for the allergen and which of such regions would cause the release of mediators (e.g. histamine) from mast cells or basophils. Those peptide regions found to bind immunoglobulin E and cause the release of mediators from mast cells or basophils in greater than approximately 10–15% of the allergic sera tested are preferably not included in the peptide regions arranged to form recombitope peptides.

Constructing a recombitope peptide derived from phospholipase $A_2$, a major allergen from honeybee venom can be used as an illustrative example of the construction of a recombitope peptide when the protein structure of a protein antigen is known, but the T cell epitopes are unknown or ill-defined. Phospholipase $A_2$ is composed of 134 amino acids as defined by cDNA cloning (Kuchler, K. et al. *Eur. J. Biochem*. 184:249–254). This amino acid sequence can be divided into regions, each preferably containing 20 to 35 amino acid residues, each region preferably overlapping another region by about 10 amino acids (see FIG. 12). Although FIG. 12 shows the entire protein sequence of the protein divided into regions, the total sequence used to form at least one recombitope peptide can be substantially less than the entire protein sequence. To maximize the potential of including T cell epitopes in the constructed recombitope peptide, areas of overlap and length of each region can be designed to maintain the presence of T cell epitopes predicted using algorithms (Rothbard, J. and Taylor, W. R. *EMBO J*. 7:93–100 (1988); Berzofsky, J. A. *Philos Trans R. Soc. Lond*. 323:535–544 (1989)). Preferably, human T cell epitopes within a protein allergen can be predicted using known HLA class II specific binding specific amino acid residues. Furthermore, to minimize the likelihood that the constructed recombitope peptide will bind human allergic IgE, the amino acid sequence of the resulting recombitope peptide can be made different from that of the native structure of phospholipase $A_2$ by scrambling the regions and/or by transposing amino terminal regions or carboxy terminal regions to the opposite end of the molecule (i.e., amino acid residues located at the amino terminus of the native protein can be placed in the carboxy terminus of the recombitope peptide). A similar procedure can be utilized to construct a recombitope peptide derived from an autoantigen with a known protein structure, but with undefined T cell epitopes such as glutamic acid decarboxylase (e.g., Samama, J. P., and Mallet, J. *Journal of Neurochemistry* 54:703–705 (1990)), insulin (*Joslin's Diabetes Mellitus*, 12th Edition, Eds. A. Marble et al., Lea & Febiger, Philadelphia, p. 67 (1985)), , etc. In this situation, the peptide regions are arranged in a configuration different from a naturally-occurring configuration of the regions in the autoantigen to eliminate an undesired property of the autoantigen such as immunoglobulin binding or enzymatic activity.

Recombitope peptides comprising at least two regions derived from an allergen or other antigen are tested to determine those recombitope peptides having T cell stimulating activity (i.e., proliferation, lymphokine secretion and/or induction of T cell anergy/tolerization) and thus comprise at least one T cell epitope. For example, human T cell stimulating activity can be tested by culturing T cells obtained from an individual sensitive to a protein allergen or protein antigen (i.e., an individual who has an immune response to the protein allergen or protein antigen) with a recombitope peptide derived from the protein allergen or antigen and determining the presence of proliferation by the T cells in response to the recombitope peptide. As described in detail in the Examples, stimulation indices for responses by T cells to recombitope peptides can be calculated as the maximum CPM in response to recombitope peptide divided by the medium control CPM. As used throughout this application, human T cell stimulating activity is defined as a stimulation index of at least 2.0. A stimulation index of at least 2.0 is considered positive for purposes of defining recombitope peptides useful as immunotherapeutic agents. Preferred recombitope peptides have a stimulation index of at least 2.5, more preferably at least 3.5, and most preferably at least 5.0.

In addition, preferred recombitope peptides of the invention derived from protein allergens do not bind immunoglobulin E (IgE) or bind IgE to a substantially lesser extent than the protein allergen(s) from which the peptides are derived binds IgE. The major complications of standard immunotherapy are systemic responses such as anaphylaxis. Immunoglobulin E is a mediator of anaphylactic reactions which result from the binding and cross-linking of antigen to IgE on mast cells or basophils and the release of mediators (e.g., histamine, serotonin, eosinophil chemotactic factors). Thus, anaphylaxis could be avoided by the use of a recombitope peptide which does not bind IgE, or if the recombitope peptide binds IgE, such binding does not result in the release of mediators (e.g., histamine, etc.) from mast cells or basophils. In addition, recombitope peptides which have minimal IgE stimulating activity are particularly desirable for therapeutic effectiveness. Minimal IgE stimulating activity refers to IgE production that is less than the amount of IgE production and/or IL-4 production stimulated by the whole protein allergen.

A recombitope peptide of the invention derived from a protein allergen, when administered to an individual sensitive to the protein allergen, is capable of modifying the allergic response of the individual to the allergen. Particularly, recombitope peptides comprising at least two T cell epitopes of a protein allergen or at least two regions derived from a protein allergen, each region preferably comprising at least one T cell epitope, when administered to an individual sensitive to the allergen are capable of modifying T cell response of the individual to the allergen. As used herein, modification of the allergic response of an individual sensitive to a protein allergen can be defined as non-responsiveness or diminution in symptoms to the allergen, as determined by standard clinical procedures (see e.g., Varney et al., *British Medical Journal* 302: 265–269 (1990)).

As a result of the work described herein, recombitope peptides derived from protein allergens or other protein antigens and having T cell stimulating activity or preferably comprising two regions each having at least one T cell epitope have been produced. T cell epitopes are believed to be involved in initiation and perpetuation of the immune response to a protein allergen or other protein antigen which is responsible respectively for the clinical symptoms of allergy or other diseases. These T cell epitopes are thought to trigger early events at the level of the T helper cell by binding to an appropriate HLA molecule on the surface of an antigen presenting cell and stimulating the relevant T cell subpopulation. These events lead to T cell proliferation, lymphokine secretion, local inflammatory reactions, recruitment of additional immune cells to the site, and activation of the B cell cascade leading to production of antibodies. One isotype of these antibodies, IgE, is fundamentally important to the development of allergic symptoms and its production is influenced early in the cascade of events, at the level of the T helper cell, by the nature of the lymphokines secreted. A T cell epitope is the basic element or smallest unit of recognition by a T cell receptor, where the epitope comprises amino acids essential to receptor recognition and may be contiguous and/or non-contiguous in the amino acid sequence of the protein. A T cell epitope, as used herein has a stimulation index of at least 2.0, more preferably at least 2.5, even more preferably at least 3.5 and most preferably at least 5.0. Amino acid sequences which mimic those of the T cell epitopes and which modify the allergic response to protein allergens are within the scope of this invention.

Exposure of patients to recombitope peptides of the present invention derived from protein allergens or other protein antigens may tolerize or anergize appropriate T cell subpopulations such that they become unresponsive to the protein allergen or other antigen and do not participate in stimulating an immune response upon such exposure. In addition, administration of a recombitope peptide of the present invention derived from a protein allergen may modify the lymphokine secretion profile as compared with exposure to the naturally-occurring protein allergen or portion thereof (e.g., result in a decrease of IL-4 and/or an increase in IL-2). Furthermore, exposure to the recombitope peptide may influence T cell subpopulations which normally participate in the response to the allergen such that these T cells are drawn away from the site(s) of normal exposure to the allergen (e.g., nasal mucosa, skin, and lung) towards the site(s) of therapeutic administration of the recombitope peptide. This redistribution of T cell subpopulations may ameliorate or reduce the ability of an individual's immune system to stimulate the usual immune response at the site of normal exposure to the allergen, resulting in a diminution in allergic symptoms.

Recombitope peptides of the invention preferably comprise at least two T cell epitopes (e.g., the recombitope peptide comprises at least approximately eight amino acid residues, and preferably at least fifteen amino acid residues). Other recombitope peptides of the invention comprise at least two regions derived from the same or from different protein allergens or other protein antigens, said recombitope peptides having T cell stimulating activity and each region preferably having human T cell stimulating activity and accordingly comprising at least one T cell epitope of a protein allergen or other protein antigen. In general, each such region of a recombitope peptide comprises at least approximately seven amino acid residues of at least one protein allergen. Each such region of a recombitope peptide preferably comprise at least two T cell epitopes (e.g., the recombitope peptide comprises at least approximately eight amino acid residues and preferably at least fifteen amino acid residues). Recombitope peptides of the invention can comprise as many amino acid residues as desired and preferably comprise at least about 7, more preferably at least about 15, even more preferably at least about 30 and most preferably at least about 40 amino acid residues of a protein allergen or other protein antigen. A region of a recombitope peptide preferably comprises up to 45 amino acid residues in length, more preferably up to 40 amino acid residues in length, and most preferably up to 30 amino acid residues in length, as increases in length of a region of a recombitope peptide may result in difficulty in peptide synthesis as well as retention of an undesirable property (e.g., immunoglobulin binding or enzymatic activity) due to maintenance of conformational similarity between the region and the protein allergen or other protein antigen from which it is derived. If desired, the amino acid sequences of the regions can be produced and joined by a linker to increase sensitivity to processing by antigen-presenting cells. Such linker can be any non-epitope amino acid sequence or other appropriate linking or joining agent.

When recombitope peptides are derived from protein allergens, they can comprise at least two regions derived from different protein allergens from the same genus, such as: the genus *Dermatophagoides;* the genus *Felis;* the genus *Ambrosia;* the genus *Lolium;* the genus *Cryptomeria;* the genus *Alternaria;* the genus *Alder;* the genus *Betula;* the genus *Quercus;* the genus *Olea;* the genus *Artemisia;* the genus *Plantago;* the genus *Parietaria;* the genus *Canine;* the genus *Blattella,* the genus *Apis;* and the genus *Periplaneta.* In addition, recombitope peptides can comprise at least two regions derived from cross-reactive species, for example one region derived from *Dermatophagoides pteronyssinus* and one region derived from *Dermatophagoides farinae.* In another embodiment, the regions can be derived from the same species (e.g., one region derived from Der p I and one region derived from Der p II; one region derived from Der f I and one region derived from Der f II; one region derived from Amb a I and one region derived from Amb a II; one region derived from Lol p I and one region derived from Lol p IX; and one region derived from Cry j I and one region derived from Cry j II). Furthermore, recombitope peptides can comprise at least two regions derived from different protein allergens from the same group, such as one region derived from a group I protein allergen of *Dermatophagoides pteronyssinus* (i.e., Der p I) and one region derived from a group I protein allergen of *Dermatophagoides farinae* (i.e., Der f I). Alternatively, the regions can be derived from different protein allergens from the same family (e.g., Amb a I.1, Amb a I.2, Amb a I.3, and Amb a I.4). Particularly preferred recombitope peptides are derived from the genus Felis and comprise regions selected from peptides X, Y, Z, A and B, of TRFP, the amino acid sequences of each peptide as shown in FIG. 4. Preferred recombitope peptides comprise peptide YZX and peptide AYZXB. Throughout the application, the letters X, Y, Z, A and B refer respectively to peptide X, peptide Y, peptide Z, peptide A and peptide B and when the letters are used together (e.g., YZX), we are referring to a recombitope peptide comprising peptide Y, peptide Z and peptide X in the sequential order specified (i.e., YZX refers to a recombitope peptide comprising the amino acid sequence of peptide Y followed immediately, without any intervening amino acid residues, by the amino acid sequence of peptide Z followed immediately, without any intervening amino acid residues, by the amino acid sequence of peptide X). The recombitope peptides of the invention, e.g., YZX, can comprise additional amino acid residues of either the amino or carboxy terminus of the recombitope peptide.

Recombitope peptides of the invention can be derived from protein antigens other than protein allergens where enhancement or depression of an antigen specific immune response is desired. For example, regions having human T cell stimulating activity of a known autoantigen involved in the pathogenesis of an autoimmune disease or T cell epitopes of a known autoantigen can be identified and combined in a recombitope peptide to decrease the antibody response to the autoantigen, to interfere with efficacy and/or decrease immune complex related side effects. In order to preserve the T cell reactivity of the autoantigen, regions of the autoantigen having human T cell stimulating activity could be defined by standard T cell biology techniques, or if desired, precise T cell epitopes can be defined by fine mapping techniques and a recombitope peptide comprising at least two regions each having human T cell stimulating activity and comprising at least one T cell epitope produced. For example, if three regions having human T cell stimulating activity or three T cell epitopes were found in an autoantigen in a sequential and contiguous order 1, 2, 3 from an amino terminus to a carboxy terminus, six possible recombitope peptides utilizing each region or each T cell epitope once could be produced comprising the three regions or T cell epitopes in various orders (e.g., 213, 312, 132, 321, 123, 231). These six recombitope peptides could be tested for the ability to stimulate T cell activity and for the absence of an undesired property present in the autoantigen, e.g., the inability of the recombitope peptide(s) to bind autoantibodies. Alternatively, as described previously, recombitope peptides can be constructed from an autoantigen without knowing which regions have T cell stimulating activity or what the precise T cell epitopes are. The recombitope peptides which stimulate T cells and do not have undesired properties of the autoantigen (e.g., do not bind autoantibodies in a substantial percentage of individuals sensitive to the autoantigen) are selected for use as immunotherapeutics or diagnostic agents. In the form of a therapeutic composition, the recombitope peptide would be delivered in a physiologically acceptable vehicle in the absence of adjuvant to allow the recombitope peptide to induce antigen specific tolerance to the autoantigen from which the recombitope is derived and regulate any potentially damaging immune response. Among autoantigens useful in producing recombitope peptides are insulin, glutamic acid decarboxylase (64K), PM-1 and carboxypeptidase in diabetes; myelin basic protein in multiple sclerosis; rh factor in erythroblastosis fetalis; acetylcholine receptors in myasthenia gravis; thyroid receptors in Graves' Disease; basement membrane proteins in Good Pasture's syndrome; and thyroid proteins in thyroiditis.

Recombitope peptides within the scope of the invention can be used in methods of treating and diagnosing sensitivity in an individual to a protein allergen or other protein antigen. Thus, one aspect of the invention provides therapeutic compositions comprising a recombitope peptide and a pharmaceutically acceptable carrier or diluent. Administration of the therapeutic compositions of the present invention to desensitize an individual to a protein allergen or other protein antigen can be carried out using known techniques. For example, a recombitope peptide can be administered in combination with an appropriate diluent, a carrier, and/or an adjuvant, where appropriate. Pharmaceutically acceptable diluents include saline and aqueous buffer solutions. Pharmaceutically acceptable carriers include polyethylene glycol (Wie et al., *International Archives of Allergy and Applied Immunology* 64: 84–99 (1981)) and liposomes (Strejan et al., *Journal of Neuroimmunology* 7: 27 (1984)). Pharmaceutically acceptable adjuvants include alum. Such compositions will generally be administered by injection, oral administration (e.g., as in the form of a capsule), inhalation, transdermal application or rectal administration. The therapeutic compositions of the invention are administered to individuals sensitive to an allergen or other protein antigen from which the recombitope peptide is derived, at dosages and for lengths of time effective to reduce sensitivity of the individual to the allergen or other antigen. A therapeutically effective amount of one or more of the same or of different therapeutic compositions can be administered simultaneously or sequentially to an individual sensitive to an allergen or other protein antigen. Effective amounts of the therapeutic compositions will vary according to factors such as the degree of sensitivity of the individual, the age, sex, and weight of the individual, and the ability of the peptides to stimulate a T cell response in the individual. In yet another aspect of the present invention, a composition is provided comprising at least two recombitope peptides (e.g., a physical mixture of at least two recombitopes), each comprising at least two T cell epitopes derived from the same or from different protein allergens or other protein antigens.

The present invention also provides methods of detecting sensitivity in individuals to a protein antigen and methods of determining the presence of immunoglobulin specific for a protein antigen and the ability of T cells of individuals to respond to the antigen. In order to detect sensitivity, a blood sample obtained from the individual or at least one portion of the sample is combined with a protein antigen, modified form of the protein antigen, or a portion of either antigen, each of which binds immunoglobulin specific for the antigen, under conditions appropriate for binding of blood components with the antigen, modified antigen or portion thereof. A second blood sample obtained from an individual found to have binding of blood components with the protein antigen, modified antigen or portion thereof, or a second portion of the first blood sample from an individual found to have binding of blood components with the protein antigen, modified antigen or portion thereof, is combined with a recombitope peptide comprising at least two regions derived from a protein antigen, said recombitope peptide having T cell stimulating activity; or a recombitope peptide comprising at least two regions derived from a protein antigen, each region which has human T cell stimulating activity; or a modified form of the protein antigen or a portion thereof; or the protein antigen produced recombinantly, each of which does not bind immunoglobulin specific for the protein antigen in a substantial percentage of the population of individuals sensitive to the protein antigen (e.g., at least about 75%), in order to determine whether T cell stimulation occurs. If the protein antigen is a protein allergen, then the modified form of the protein allergen or a portion thereof, the recombinantly produced protein allergen, or the recombitope peptide derived from the protein allergen does not bind IgE specific for the protein allergen, or if binding of IgE occurs, such binding does not result in release of mediators from mast cells or basophils in a substantial percentage of a population of individuals sensitive to the allergen. If the individual is found to have binding of blood components to the antigen, modified antigen or portion thereof and T cell stimulation in response to the recombitope peptide, modified protein antigen, or portion thereof or recombinantly produced protein antigen, then the individual can be administered a therapeutically effective amount of a therapeutic composition comprising the recombitope peptide, recombinantly produced protein antigen, or the modified form of the protein antigen or portion thereof, and a pharmaceutically acceptable carrier or diluent to desensitize the individual to the protein antigen.

The present invention also provides methods for detecting specific Delayed Type Hypersensitivity in an individual to at least one protein allergen. According to the method, an individual is administered a Delayed Type Hypersensitivity test (See e.g., *Immunology* (1985) Roitt, I. M., Brostoff, J., Male, D. K. (eds), C. V. Mosby Co., Gower Medical Publishing, London, N.Y., pp. 19.2–19.18; pp. 22.1–22.10) utilizing a modified form of the protein allergen or other protein antigen or a portion thereof, or a protein allergen or other protein antigen produced recombinantly, or a recombitope peptide derived from said at least one protein allergen or other protein antigen, each of which has human T cell stimulating activity and each of which does not bind immunoglobulin specific for the protein allergen or other protein antigen in a substantial percentage (e.g., at least about 75%) of individuals sensitive to said protein allergen or other protein antigen. If the protein antigen is a protein allergen, then the modified form of the protein allergen or a portion thereof, the recombinantly produced protein allergen, or the recombitope peptide derived from the protein allergen does not bind IgE specific for the protein allergen, or if binding of IgE occurs, such binding does not result in release of mediators from mast cells or basophils in a substantial percentage of a population of individuals sensitive to the allergen. It has been found that recombinant chain 1 of TRFP in a dimeric form has markedly reduced IgE binding, but maintains T cell reactivity (i.e., recombinant dimeric chain 1 contains peptides X and Y, both of which are known to contain at least one T cell epitope) and that mild alkali treated TRFP has markedly reduced IgE binding, but maintains T cell reactivity. Accordingly, recombinant chain 1 of TRFP in dimeric form or alkali treated TRFP could be used in the Delayed Type Hypersensitivity test described above, or in other diagnostic assays to determine sensitivity in an individual to T cell epitope(s) of TRFP and/or they can be used in therapeutic compositions to desensitize individuals to TRFP. After administration of the Delayed Type Hypersensitivity test, the extent to which a specific Delayed Type Hypersensitivity reaction occurs in the individual to the protein allergen or other protein antigen indicating presence in the individual of T cells specific to T cell epitope(s) of the protein allergen or other protein antigen is determined.

The present invention further provides methods of detecting and treating sensitivity in an individual to at least one protein allergen. The presence in individuals of IgE specific for at least one protein allergen and the ability of T cells of the individuals to respond to T cell epitope(s) of the protein allergen can be determined by administering to the individuals an Immediate Type Hypersensitivity test and a Delayed Type Hypersensitivity test. The individuals are administered an Immediate Type Hypersensitivity test (See e.g., *Immunology* (1985) Roitt, I. M., Brostoff, J., Male, D. K. (eds), C. V. Mosby Co., Gower Medical Publishing, London, N.Y., pp. 19.2–19.18; pp. 22.1–22.10) utilizing the protein allergen or a portion thereof, or a modified form of the protein allergen or a portion thereof, each of which binds IgE specific for the allergen. The same individuals are administered a Delayed Type Hypersensitivity test prior to, simultaneously with, or subsequent to administration of the Immediate Type Hypersensitivity test. Of course, if the Immediate Type Hypersensitivity test is administered prior to the Delayed Type Hypersensitivity test, the Delayed Type Hypersensitivity test would be given to those individuals exhibiting a specific Immediate Type Hypersensitivity reaction. The Delayed Type Hypersensitivity test utilizes a modified form of the protein allergen or a portion thereof, the protein allergen produced recombinantly, or a recombitope peptide derived from the protein allergen, each of which has human T cell stimulating activity and each of which does not bind IgE specific for the allergen in a substantial percentage of the population of individuals sensitive to the allergen (e.g., at least about 75%). Those individuals found to have both a specific Immediate Type Hypersensitivity reaction and a specific Delayed Type Hypersensitivity reaction are administered a therapeutically effective amount of a therapeutic composition. The therapeutic composition comprises the modified form of the protein or portion thereof, the recombinantly produced protein allergen, or the recombitope peptide, each as used in the Delayed Type Hypersensitivity test, and a pharmaceutically acceptable carrier or diluent.

It is also possible to modify the structure of recombitope peptides for such purposes as increasing solubility, enhancing therapeutic or preventive efficacy, or stability (e.g., shelf life ex vivo, and resistance to proteolytic degradation in vivo). A modified recombitope peptide can be produced in which the amino acid sequence has been altered, such as by amino acid substitution, deletion, or addition, to modify immunogenicity and/or reduce allergenicity, or to which a component has been added for the same purpose. For example, the amino acid residues essential to T cell epitope function can be determined using known techniques (e.g., substitution of each residue and determination of presence or absence of T cell reactivity). Those residues shown to be essential can be modified (e.g., replaced by another amino acid whose presence is shown to enhance T cell reactivity), as can those which are not required for T cell reactivity (e.g., by being replaced by another amino acid whose incorporation enhances T cell reactivity but does not diminish binding to relevant MHC). Another example of a modification of recombitope peptides is substitution of cysteine residues preferably with alanine, or glutamic acid, or alternatively with serine or threonine to minimize dimerization via disulfide linkages. In order to enhance stability and/or reactivity, recombitope peptides can also be modified to incorporate one or more polymorphisms in the amino acid sequence of a protein allergen resulting from natural allelic variation. Additionally, D-amino acids, non-natural amino acids or non-amino acid analogues can be substituted or added to produce a modified peptide within the scope of this invention. Furthermore, recombitope peptides can be modified using the polyethylene glycol (PEG) method of A. Sehon and co-workers (Wie et al. supra) to produce a peptide conjugated with PEG. Modifications of recombitope peptides can also include reduction/alkylation (Tarr in: *Methods of Protein Microcharacterization*, J. E. Silver ed. Humana Press, Clifton, N.J., pp 155–194 (1986)); acylation (Tarr, supra); esterification (Tarr, supra); chemical coupling to an appropriate carrier (Mishell and Shiigi, eds, *Selected Methods in Cellular Immunology*, WH Freeman, San Francisco, Calif. (1980); U.S. Pat. No. 4,939,239); or mild formalin treatment (Marsh *International Archives of Allergy and Applied Immunology* 41: 199–215 (1971)).

To facilitate purification and potentially increase solubility of recombitope peptides, it is possible to add reporter group(s) to the peptide backbone. For example, poly-histidine can be added to a recombitope peptide to purify the recombitope peptide on immobilized metal ion affinity chromatography (Hochuli, E. et al., *Bio/Technology*, 6:1321–1235 (1988)). In addition, specific endoprotease cleavage sites can be introduced, if desired, between a reporter group and amino acid sequences of a recombitope peptide to facilitate isolation of recombitope peptides free of irrelevant sequences. In order to successfully desensitize an individual to a protein antigen, it may be necessary to increase the solubility of a recombitope peptide by adding functional groups to the peptide or by not including hydrophobic T cell epitopes or regions containing hydrophobic epitopes in the recombitope peptides.

To potentially aid proper antigen processing of T cell epitopes within a recombitope peptide, canonical protease sensitive sites can be recombinantly or synthetically engineered between regions, each comprising at least one T cell epitope. For example, charged amino acid pairs, such as KK or RR, can be introduced between regions within a recombitope peptide during recombinant construction of the recombitope peptide. The resulting recombitope peptide can be rendered sensitive to cathepsin and/or other trypsin-like enzymes cleavage to generate portions of the recombitope peptide containing one or more T cell epitopes. In addition, such charged amino acid residues can result in an increase in solubility of a recombitope peptide.

Site-directed mutagenesis of DNA encoding a recombitope peptide can be used to modify the structure of the recombitope peptide. Such methods may involve PCR (Ho et al., *Gene* 77:51–59 (1989)) or total synthesis of mutated genes (Hostomsky, Z., et al., *Biochem. Biophys. Res. Comm.* 161:1056–1063 (1989)). To enhance bacterial expression, the aforementioned methods can be used in conjunction with other procedures to change the eucaryotic codons in DNA constructs encoding recombitope peptides to ones preferentially used in *E. coli*.

The present invention also provides nucleic acid sequences coding for recombitope peptides of the invention. Nucleic acid sequences used in any embodiment of this invention can be cDNA as described herein, or alternatively, can be any oligodeoxynucleotide sequence having all or a portion of a sequence represented herein, or their functional equivalents. Such oligodeoxynucleotide sequences can be produced chemically or mechanically, using known techniques. A functional equivalent of an oligonucleotide sequence is one which is 1) a sequence capable of hybridizing to a complementary oligonucleotide to which the oligonucleotide sequence (or corresponding sequence portions) or fragments thereof hybridizes, or 2) the sequence (or corresponding sequence portion) complementary to the oligonucleotide sequence and/or 3) a sequence which encodes a product (e.g., a protein, a polypeptide or a peptide) having the same functional characteristics of the product encoded by the oligonucleotide sequence (or corresponding sequence portion). Whether a functional equivalent must meet one or more criteria will depend on its use (e.g., if it is to be used only as a probe for hybridization, it need meet only the first or second criteria and if it is to be used to produce a peptide of the present invention, it need only meet the third criterion).

Figure 11:
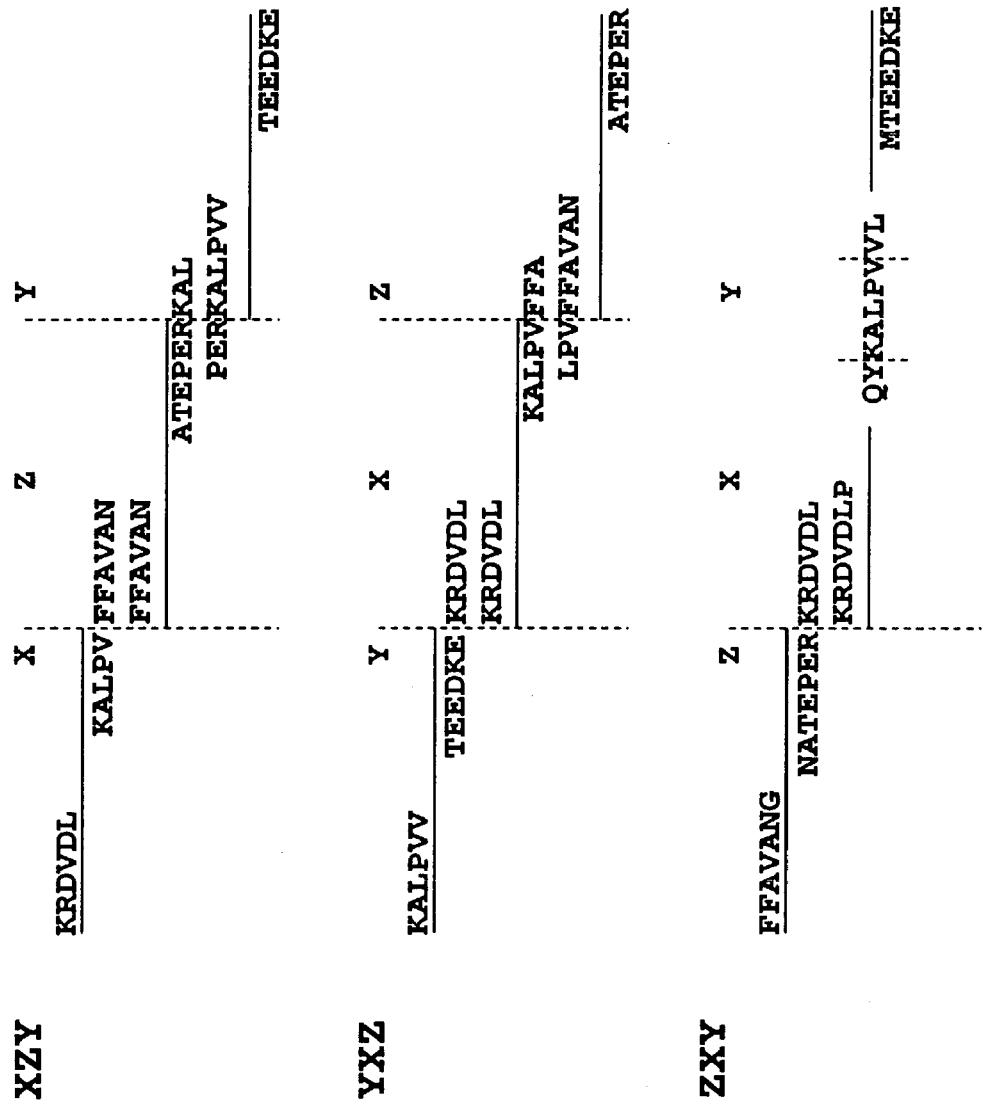
FIG. 11 is a graphic depiction of the amino acid sequence of the individual primers used to construct the recombitope peptides XZY, YXZ and ZXY.

As described in the Examples which follow, chains 1 and 2 of the human T cell Reactive Feline Protein (TRFP) (FIGS. 1 and 2) have been recombinantly expressed in *E. coli* and purified. T cell epitope studies using overlapping peptide regions derived from the TRFP amino acid sequence were used to identify multiple T cell epitopes in each chain of TRFP. As described in detail in Example 2, DNA constructs were assembled in which three regions (designated peptide X, peptide Y and peptide Z), each containing at least one major human T cell epitope of TRFP were linked in six possible combinations to produce six DNA constructs encoding recombitope peptides comprising the three regions in six different configurations. Since peptide X shares 5 amino acids at its carboxy terminus with 5 amino acids at the amino terminus of peptide Y, recombitope peptides XYZ and ZXY could have been constructed with or without duplication of said 5 amino acids (See FIG. 11 where ZXY is constructed without duplication of the 5 amino acid sequence). In the following Examples, the recombitope peptides were assembled contiguously, without duplication of the 5 amino acid sequence. In addition to the three regions X, Y and Z, other regions, each containing at least one human T cell epitope, could also be included in the recombitope peptides and DNA constructs having four or more regions (of N! configurations, where N=the number of regions) produced. Alternatively, one or more regions can be substituted for peptide X, peptide Y, or peptide Z, such as peptide A or B as shown in FIG. 4, to produce for example recombitope peptide AXY.

Detailed protocols are described for the cleavage and removal of extraneous sequences added to recombitope peptides as an aid to purification. Purified recombitope peptides have been examined for the binding of human cat-allergic patients' IgE on Western blots and compared to IgE binding of recombinant chains 1 and 2 of TRFP. An ELISA was performed to examine allergic IgE binding to recombitope peptides relative to native TRFP, recombinant chain 1, and recombinant chain 2. The work described herein demonstrates that recombitope peptides of the present invention have T cell stimulating activity even though their epitope configuration generally differs from that found in the native TRFP protein sequence. Furthermore, use of the recombitope peptides as prophylactic agents has been shown to render mice unresponsive upon antigen challenge with native TRFP, recombinant chain 1, or chain 2 of TRFP, or the recombitope peptide used.

This invention is further illustrated by the following non-limiting examples.

EXAMPLE 1

T CELL EPITOPE STUDIES WITH OVERLAPPING TRFP PEPTIDES

Peripheral blood mononuclear cells (PBMC) were purified by Ficoll-Hypaque centrifugation of 60 ml of heparinized peripheral blood from cat-allergic patients, who exhibited clinical symptoms of cat allergy and who were skin test positive with cat extract. Ten million PBMC from an individual patient were cultured in 10 ml RPMI-1640 (Gibco) containing 5% pooled human AB serum and supplemented with glutamine, penicillin, streptomycin and HEPES buffer (complete RPMI-1640) in the presence of 20 1 g native affinity-purified TRFP/ml of culture at 37° C. for 7 days. Viable cells were then purified by Ficoll-Hypaque centrifugation and cultured for 2 additional weeks in complete RPMI-1640 containing 5 units recombinant human IL-2/ml and 5 units recombinant human IL-4/ml. The resting T cells resulting from the culture were then tested in a secondary proliferation assay using a 96 well microtiter plate to assess T cell responses to the various TRFP peptides or proteins (TRFP antigens) as shown in FIG. 3 . For assay, $2\times10^4$ resting T cells were cultured in complete RPMI-1640 for 3 days at 37° C. in the presence of $5\times10^4$ autologous PBMC (3500 Rads) as antigen presenting cells with a various concentration of one of the TRFP antigens in each well in the amount of 200 11 per well. Each well then received 1 1 Ci tritiated thymidine for 16 hours. The counts incorporated were collected onto glass fiber filters and processed for liquid scintillation counting. The stimulation indices for responses to each peptide were then calculated as the maximum CPM in response to antigen divided by the medium control CPM. A stimulation index of 2.5 was considered to be a positive T cell response. (As used throughout this application, human T cell stimulating activity is defined as a stimulation index of at least 2.0. However, the stimulation index of the T cell epitopes or regions to be used in producing a recombitope of the invention is at least 2.0, preferably at least 2.5, more preferably at least 3.5 and most preferably at least 5.0.) A summary of the results of 34 such experiments is shown in FIG. 3. The top five peptide responses to the overlapping set of TRFP peptides covering chain 1 and chain 2 of TRFP by the T cell line derived from each patient were ranked, assigning the highest positive response a 5, the next highest positive a 4, and so on. The sum of the ranks obtained for each peptide was then calculated and is displayed on the histogram in FIG. 3. This type of analysis highlights the relative importance of different regions of the TRFP molecule in the T cell response to the intact protein. The results indicate that the major regions of T cell reactivity in this panel of patients are encompassed (in order of importance) by Fel-14.2 (chain 1, amino acid residues 29–42), Fel-3.1 (chain 1, amino acid residues 18–32), Fel-2 (chain 1, amino acid residues 9–25), Fel-21 (chain 1, amino acid residues 56–70), Fel-29 (chain 1, amino acid residues 56–70), Fel-1.2 (chain 1, amino acid residues 1–17), Fel-4 (chain 1, amino acid residues 37–55), Fel-18 (chain 2, amino acid residues 23–48), Fel-25 (chain 2, amino acid residues 49–68) Fel-16 (chain 2, amino acid residues 1–22) and Fel 23 (chain 1, amino acid residues 51–66). A set of peptides was then designed to cover these regions. Portions of Fel-1.2, Fel-2, Fel-3.1 and Fel-14.2 comprise peptide X (chain 1 amino acid residues 7–33). Portions of Fel-3. 1, Fel-14.2, and Fel-4 comprise peptide Y (chain 1, amino acid residues 29–55). Portions of Fel-16, Fel-17 and Fel-18 comprise peptide Z (chain 2, amino acid residues 14–39). Portions of Fel-4, Fel 21 and Fel-23 comprise peptide A. Portions of Fel-29 comprise peptide B. Peptides X, Y, Z, A and B are shown in FIG. 4.

EXAMPLE 2

CONSTRUCTION AND EXPRESSION OF RECOMBITOPE PEPTIDES

PCR methods (Polymerase Chain Reaction) using synthetic oligonucleotides were used to construct DNAs encoding the sequences of peptides X, Y, and Z. With the aim of enhancing expression in *E. coli*, the codons in the oligonucleotides were selected from a table of those prevalent in highly expressed *E. coli* proteins. Sharp, P. M., et al., *Nucl. Acids Res*. 16:8207 (1988). The oligonucleotides and PCR procedures used to construct recombitope peptides are described in detail below.

Oligonucleotides were designed with *E. coli* preferred codons as schematically represented in FIGS. 5 and 6. These oligonucleotides (C,D,E,F,G,H,I,J,K,L,M,N and O shown in FIG. 7), were amplified using a Perkin Elmer/Cetus GeneAmp kit, in two separate PCR reactions (PCR#1 and PCR#2, respectively wherein PCR #1 resulted in the synthesis of the 5' portion of the DNA molecule encoding the recombitope peptide and PCR #2 resulted in the synthesis of the 3' portion of the DNA molecule encoding the recombitope peptide). This approach was taken due to the presence of a sequence (KALPV) in both peptide X and peptide Y that was found to interfere in the proper PCR generation of recombitope YZX when a single PCR reaction was performed with oligonucleotides (C—I). In producing recombitope peptide AYZXB, as shown in FIG. 6, the oligonucleotides used in PCR #1 were N,J,K, and C—I and the oligonucleotides used in PCR #2 were C—I and L,M,O. In producing recombitope peptide YZX, as shown in FIG. 5, the oligonucleotides used in PCR #1 were C,D E and F, whereas the oligonucleotides used in PCR #2 were F, G, H and I. Each reaction mixture (10 Tg) generated the 5' half and 3' half respectively, of the intended YZX structure (FIG. 5). These PCR mixtures, after the addition of Taq polymerase, were subjected to the following program with cycles of denaturation, annealing and polymerization:

| STEP # | TEMPERATURE | TIME |
|---|---|---|
| 1 | 94° C. | 1 MINUTE |
| 2 | 50° C. | 1.5 MINUTES |
| 3 | 75° C. | 2 MINUTES |
| 4 | REPEAT STEPS 1–3 (4 TIMES) | |
| 5 | 94° C. | 1 MINUTE |
| 6 | 60° C. | 1.5 MINUTE |
| 7 | 75° C. | 2 MINUTES |
| 8 | REPEAT STEPS 5–7 (20 TIMES) | |
| 9 | HOLD AT 4° C. | |

After completion of the PCR#1 and PCR#2 reactions in the construction of the YZX structure, aliquots from each (100 p moles of the 10 Tg total reaction mixture; 1/100 volume) were added to a third PCR reaction mixture containing a set of 5' and 3' primers (100 p mole of primers C and I). A third PCR reaction (PCR #3) was performed utilizing this third PCR reaction mixture as previously described for PCR reactions #1 and #2 except that the annealing temperature in Step 6 was raised to 65° C. The completion of PCR#3 produced the DNA encoding recombitope peptide YZX. The PCR#3 reaction method is similar to that described in Horton, R. M., et al. *Gene* 77:61 (1989). The whole reaction mixture used in PCR#3 was fractionated on a 2% agarose gel and the appropriate sized band (230 bp) was electroeluted from the gel slice and precipitated. The isolated DNA encoding recombitope peptide YZX was subjected to another PCR reaction using excess 5' and 3' amplification primers (C and I). This final product was digested with the restriction enzymes BamH I and then cloned into the vector pET11d under the transcriptional control of the phage T7 gn 10 lac 0 fusion promoter. Studier, F. W., et al. *Methods in Enzymol.* 185:60 (1990).

A polylinker encoding six sequential histidines, $(CAC)_6$, was cloned in-frame onto the 5' end of the DNA encoding recombitope peptide YZX. The six histidine ($H_6$ or $His_6$) leader sequence allowed purification of the expressed recombitope peptide using QIAGEN NTA-Agarose (Diagen Gmbh, Dusseldorf, Germany), a $Ni^{2+}$ chelating support. Hochuli, E., et al., *BioTechnology* 6:1321 (1988). DNA encoding site-specific enzymatic cleavage sites (e.g., Thrombin, Factor $X_a$, etc) can be inserted using PCR methods between the polyhistidine encoding ($H_6$) sequence and the DNA encoding the recombitope peptide backbone. In the case of recombitope peptide YZX, a thrombin recognition site (LVPRGS) was inserted. Uhlen, M., and Moks, T. *Methods in Enzymol.* 185:129 (1990), Chang, J.-Y. *Eur. J. Biochem.* 151:217 (1985).

Figure 6:
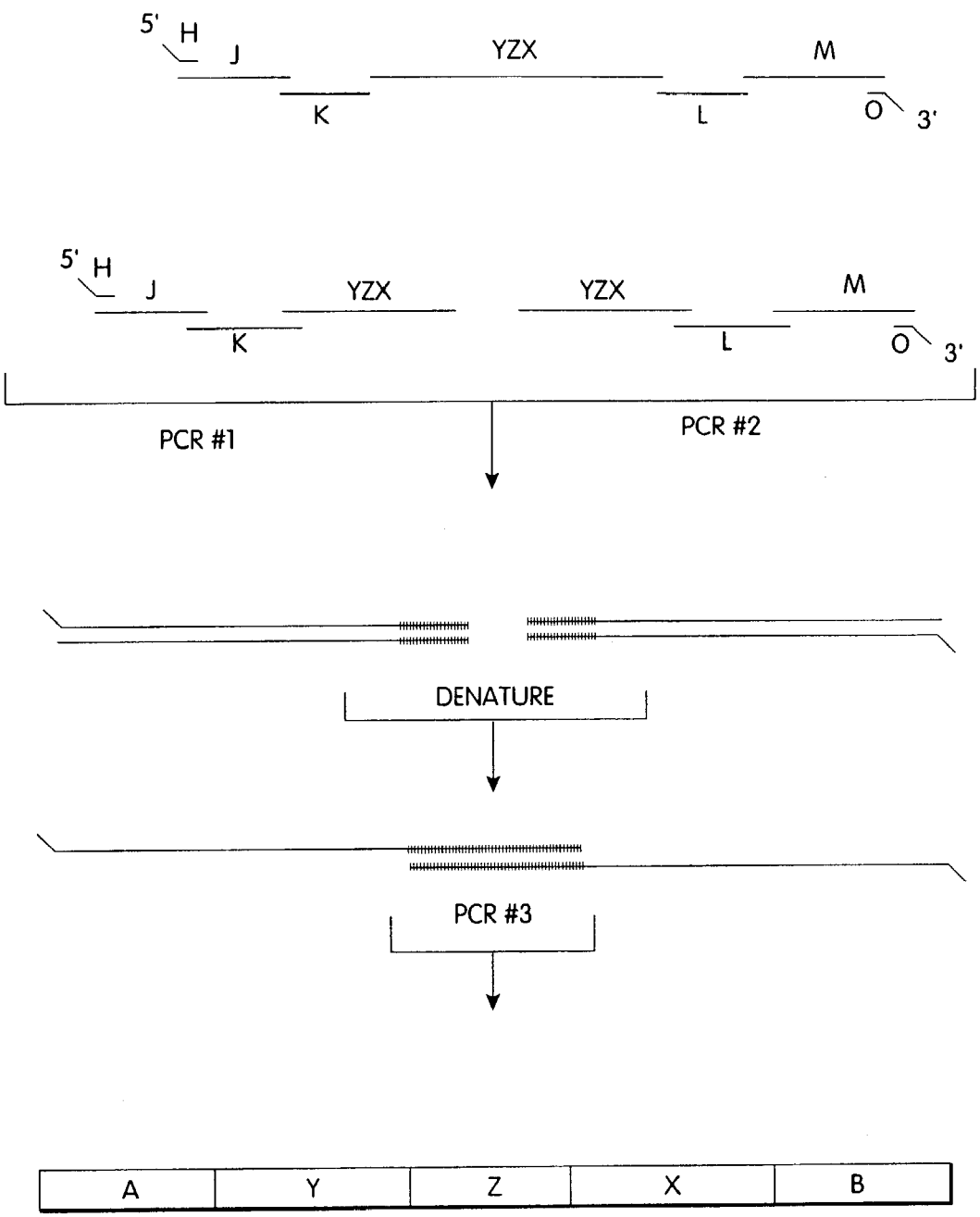
FIG. 6 is a schematic representation of the construction of a recombitope peptide AYZXB using PCR techniques.

A similar procedure to that described above to construct DNA encoding the recombitope peptide YZX was used to construct DNA encoding the recombitope peptides XYZ and ZYX. In addition, other peptides containing T cell epitopes can be added to an existing recombitope backbone structure such as YZX (as produced above) as was the case with the construction of recombitope peptide AYZXB (see FIGS. 6 and 7). Alternatively, peptides containing T cell epitopes can be produced without the use of an existing recombitope backbone using methods outlined herein. To produce recombitope peptide AYZXB, oligonucleotide primers (J-M) with overlapping regions to each end of recombitope peptide YZX and a 5' and 3' amplification primer (N and O) were produced. (As shown in FIG. 6, the darkened part of the molecule is the overlapping sequence). PCR reactions were performed as described above. The resulting AYZXB fragment was isolated and subcloned into the pET $11DH_6$ TH vector.

An alternative procedure was used to construct the DNA encoding recombitope peptides XZY, YXZ, and ZXY. Each of the DNA constructs encoding recombitope peptides XZY, YXZ and ZXY were ligated at the codon encoding the most N-terminal amino acid of the recombitope peptide with DNA encoding the leader sequence MGHHHHHHEF (where amino acids EF are encoded by the Eco RI restriction site GAATTC). DNA segments encoding the three recombitope peptides were assembled via consecutive PCR essentially as described by Horton et al., (1989) Gene 77: 61–68. The DNA segments encoding peptides X, Y, and Z (shown in FIG. 4) were amplified from the Fel d I cDNAs described in Morgenstern et al., (1991) Proc. Natl. Acad. Sci. U.S.A. 88: 9690–9694. As shown in FIG. 9, which shows as a specific example the construction of the recombitope peptide XZY coding sequence, oligonucleotide primers were synthesized with a DNA sequence that would not only amplify a specific DNA segment encoding peptide X, Y or Z, but would also covalently link a small segment (9–18 base pairs) of the DNA segment encoding the adjacent peptide X, Y, or Z. PCR was performed using Vent™ polymerase according to New England Biolabs' instructions with an amplification program of 30 X [94° C. 1 min./60° C. 1 min. 30 sec./72° C. 1 min.]. The primers used for PCR amplifications are shown in FIG. 10. Individual recombitope peptide encoding/linker DNA fragments from PCR amplifications were purified by preparative gel electrophoresis in 3% (wt./vol.) NuSieve (FMC) agarose. These individual PCR fragments were then linked in a second PCR reaction to form a DNA construct encoding XZY as shown in FIGS. 9 and 11. In order to link these PCR fragments, 3% NuSieve gel slices containing the initial PCR products were melted at 70° C., and 1 1l of each were added to a Vent™ PCR polymerase reaction which employed the 5' RI ($NH_2$-terminal) and 3' Bam (COOH-terminal) primers.

Because of the restriction sites present in the expression vector, pET11d (Studier et al, 1990), all extreme 5' primers had EcoR I encoding sites [GAATTC] in frame with the DNA encoding the $NH_2$-terminal amino acids of the particular recombitope, while the ends of the extreme 3' primers had BamH I encoding sites [GGATCC]. DNA constructs encoding recombitope peptides XZY, YXZ, and ZXY produced from the secondary PCR were EcoR I/BamH I digested and electrophoresed through a 0.5 (wt./vol.) SeaPlaque (FMC) agarose gel. Gel slices containing the DNA constructs were melted at 70° C. and added to a ligation reaction with EcoR I/BamH I digested Bluescript KS plasmid (Stratagene). The ligation was transformed into competent XL-1 Blue bacteria (Stratagene), and recombinant plasmids with inserts identified by diagnostic restriction digests after isolation using Qiatop kit (Diagen GmbH). The sequence of inserts was verified by dideoxy chain-termination sequence analysis using a Sequenase II kit (United States Biochemicals).

Bluescript KS plasmids harboring DNA constructs encoding recombitope peptides XZY, YXZ and ZXY inserts with correct nucleotide sequence were EcoR I/BamH I digested and the DNA constructs isolated from a 0.6% SeaPlaque gel for subcloning into the expression vector pET11 d in frame with the DNA encoding the $NH_2$-terminal leader MGHHHHHHEF as mentioned above. The constructs were subcloned into the EcoR I/BamH I digested pET11 d $His_6$ Amb a I.1 HR. This ligation served to exchange the DNA construct for an insert, in this case the cDNA of the major ragweed allergen, Amb a I.1 (Rafnar et al., (1991) *J. Biol. Chem*. 226:1229–1236). pET11d His Amb a I.1 -HR was derived from pET 11d in two steps. First pET11d was Eco RI/HinD III digested, blunted with Klenow fragment of *E. coli* DNA polymerase, and ligated back to itself to create pET11d -HR: a pET11d plasmid lacking Hind III and EcoR I sites. Then pET11d $His_6$Amb a I.1-HR was formed by excising the $H_6$Amb aI.1 cassette from the expression vector pET11d $His_6$Amb aI.1 as an Nco I/BamH I fragment and ligating it into Nco I/BamH I digested pET11d-HR. Recombinant plasmids were identified by diagnostic restriction digests after isolation via a Qiatip kit, and positive plasmids transformed into competent BL21 [DE3] bacteria for expression. BL21 [DE3] contains a recombinant phage 1 lysogen, DE3, with a phage T7 RNA polymerase gene under the transcriptional control of the lac UV5 promoter. T7 RNA polymerase gene expression is induced by the addition of IPTG, which in turn leads to high level expression of the recombinant gene subcloned 3' of the pET vector's T7 gn 10 lac 0 fusion promoter.

PCR-derived DNA fragments encoding ($H_6$) fusions of mature chains 1 and 2 of TRFP subcloned into pSEM (U.S. Ser. No. 662,276 filed Feb. 28, 1991) were excised and ligated into pET11d. This was achieved by attaching Bcl I linkers to the Pst I sites at the 3' ends of the two chains, Nco I digesting at the 5' end of the chains and inserting the 5' Nco I/3' Bcl I fragment into 5'Nco I/3'BamH I digested pET11d.

The recombinant peptide chains 1 and 2 of TRFP as well as the recombitope peptides XYZ, XZY, YZX, ZYX, ZXY and YXZ were expressed in E. coli and purified essentially as outlined below. BL21 DE3 host bacteria harboring the pET11d expression DNA constructs were freshly streaked onto a BHI agar plate (3.7% wt./vol. Difco Brain Heart Infusion; 1.5% wt./vol. Difco agar) supplemented with 200 1 g/ml ampicillin and incubated overnight at 37° C. A single colony was inoculated into a 2 ml of 200 1 g/ml ampicillin/BHI media (3.7% wt./vol. Difco Brain Heart Infusion) and shaken at 300 rpm at 37° C. until turbid but not saturated. The 2 ml culture was then added to 100 ml of 200 1 g/ml ampicillin/BHI media, shaken at 300 rpm at 37° C. until turbid but not saturated, at which point the culture was divided into 18×250 ml (4.5 liters) of 200 1 g/ml ampicillin/BHI media and shaken at 300 rpm at 37° C. When the $OD_{595}$ of the culture reached 1.0, expression of the recombinant peptides as $(His)_6$ fusion peptides was induced by the addition of IPTG to 400 1M, and allowed to continue for two hours.

Bacteria were harvested by centrifugation at 10,000×g for 15 minutes, and resuspended in $1/50^{th}$ volume 6 M guanidine HCl, 100 mM 2-mercaptoethanol, 100 mM $NaPO_4$, 10 mM Tris at pH 8.0. Recombinant chain 1 and chain 2 and recombitope peptides (recombinant peptides) were extracted by vigorous shaking of the resuspended bacteria for 1 hour at 25° C. This suspension was subjected to centrifugation at 15,000×g, the supernatant removed, adjusted to pH 8.0 with 10 N NaOH, and applied to an NTA agarose column that had been equilibrated in 6 M guanidine HCl, 100 mM $NaPO_4$, 10 mM Tris at pH 8.0 until the $OD_{280}$ of the effluent reached background. The column buffer was then switched to 8 M urea, 100 mM $NaPO_4$, 10 mM Tris at pH 8.0. After equilibration, a more stringent wash was performed in 8 M urea 100 mM NaOAc, 10 mM Tris pH 6.3 until the $OD_{280}$ of the effluent reached background. Each recombinant peptide (as an $His_6$ fusion) was then eluted in 8M urea 100 mM NaOAc, 10 mM Tris at pH 4.5 and collected in aliquots whose $OD_{280}$ profile was monitored. The peptide peak was dialyzed 3 times into 500 volumes of PBS (Phosphate Buffered Saline) for analysis. Yield ranged from 2 to 25 mg of recombinant peptide ($His_6$) fusion per liter with purity (as determined by densitometric scanning of SDS polyacrylamide gels) generally exceeding 90%.

The recombinant peptides (TRFP chain 1, TRFP chain 2, XYZ, YZX and ZYX) outlined above all possess an N-terminal sequence added as an aid to purification and expression (e.g., MGHHHHHL VPRGS-). This irrelevant N-terminal sequence can be removed by proteolytic digestion since the sequence contains a thrombin recognition site (LVPRGS) inserted between the polyhistidine sequence and the recombitope sequence. (See FIG. 8, the arrow indicates the thrombin cleavage site). Thrombin was used to cleave the irrelevant sequence leaving only two extra amino acid residues, GS, on the N-terminus of the TRFP chains 1 and 2 and the recombitope peptides XYZ, YZX and ZYX (Chang, J.-Y. Eur. Biochem. 151:217–224 (1985)). Efficient cleavage of the fusion protein can be achieved by using a protein to thrombin ratio of 1000 to 1 for 2 hours at 25° C. The cleavage and purification scheme used to construct recombitope peptide YZX is outlined below:

1) recombitope peptide MGHHHHH VPRGS—YZX
2) Dialyze into PBS, pH 8.0
3) Thrombin cleavage peptide: thrombin=1000:1 25° C., 2 hours
4) Reduction with 100 mM dithiothreitol in 5M guanidine HCL 37° C., 30 minutes
5) $C_4$ Reverse phase HPLC, pH 2.0
6) Lyophilization Analytical reverse-phase HPLC was performed on a VYDAC 214 TP54 column with a 42 ml bed volume. The column was loaded with 340 1 g of recombitope peptide YZX. Semi-preparative HPLC was performed using a VYDAC 214 TP 1022 column with a 95 ml bed volume loaded with 90 mg of protein. The gradient started with 0% to 30% acetonitrile containing 0.1% trifluoroacetic acid over the first 10 minutes followed by 30% to 43% acetonitrile over 15 minutes. The mobile phase was then held at 43% acetonitrile for 10 minutes. The purified recombitope peptide YZX eluted at 43% acetonitrile. The cleavage and purification were monitored by SDS-PAGE. The identification and purity of the recombitope peptide YZX was determined by protein sequence analysis using an Applied Biosystem Inc. Protein Sequenator Model 477A.

EXAMPLE 3

DIRECT BINDING ASSAY OF IgE TO TRFP PROTEINS AND RECOMBITOPES

Figure 13:
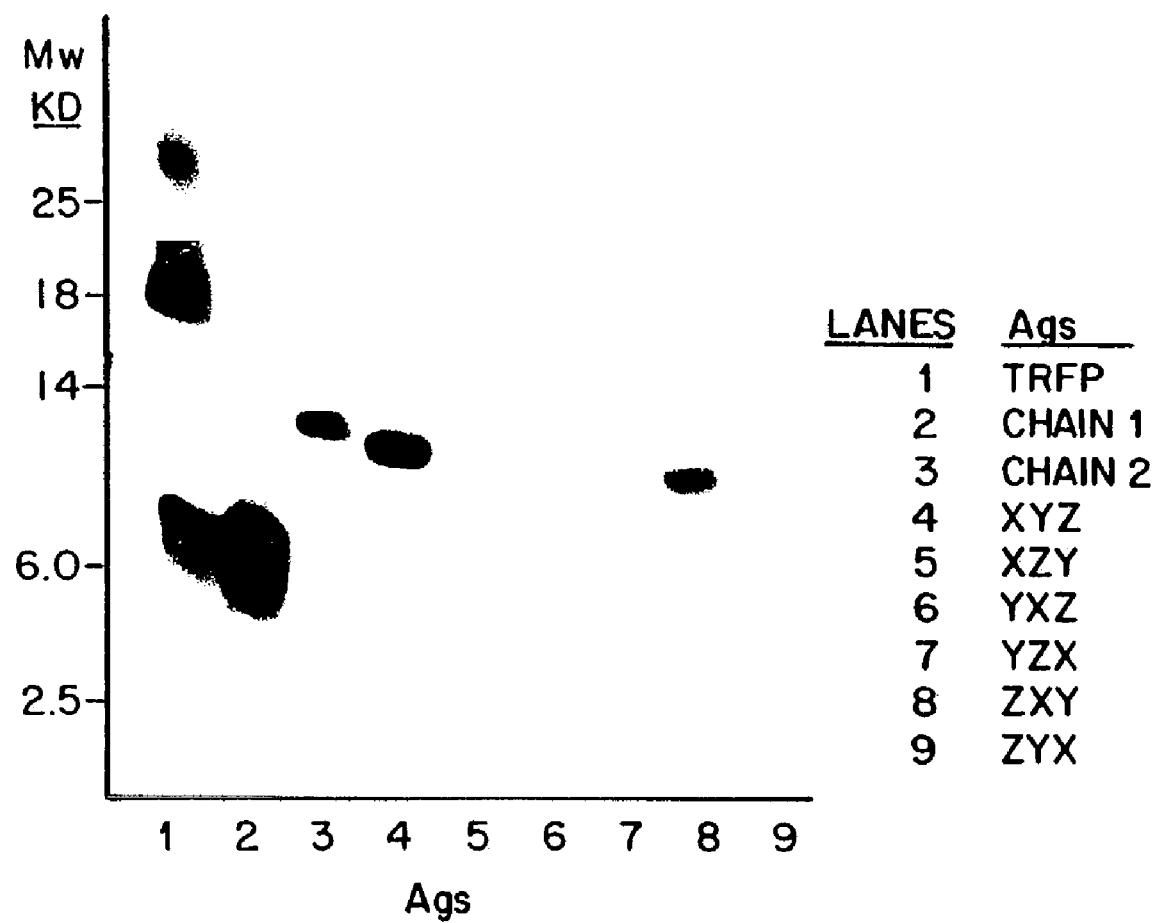
FIG. 13 is a representation of the results of SDS/PAGE Western immunoblot analysis detecting the binding of human IgE obtained from a cat allergic individual to various protein samples, including recombitope peptides XYZ, XZY, YXZ, YZX, ZXY and ZYX.

Western immunoblot analysis of the recombitope peptides produced in Example 2 was performed. The concentration of all protein samples (e.g., TRFP, recombinant chain 1 of TRFP, recombinant chain 2 of TRFP, recombitope peptide XYZ, recombitope peptide XZY, recombitope peptide YXZ, recombitope peptide YZX, recombitope peptide ZXY and recombitope peptide ZYX) for gel electrophoresis was determined by the BCA method (Pierce Co.). All protein samples were loaded on the gel at 5 Tg/lane except TRFP at 10 Tg/lane. Protein separation was carried out on a 15% acrylamide gel, and transfer was performed by electroblotting at 1.5 Amps for 1.5 hours onto nitrocellulose paper (Schleicher and Schuell, 0.1 microns) in a Hoeffer apparatus according to the protocol of Towbin, H., T. Stachlin, and J. Gordon, PNAS 76:4350 (1979). Proteins were rinsed in blot solution (25 mM Tris-HCl 7.5, 0.171 M NaCl and 0.5 ml/liter Tween 20). The blot was then blocked for one hour in blocking solution (1% milk in blot solution). Plasma from patient #417, used as a primary antibody source, was diluted in blocking solution to 10% and preabsorbed for 1.5 hours with unused nitrocellulose (2 cm×15 cm). The prepared human plasma was then incubated overnight on an orbital shaker with the protein blot section of interest. Following the first antibody incubation the blot section was washed three times, each wash involved a fifteen minute incubation in blot solution. The second antibody, specific for human IgE (biotinylated goat anti-human IgE, KPL Inc.), was diluted 1:2500 in blot solution and the incubation proceeded for two hours. Excess second antibody was subsequently removed by three 15 minute incubations with blot solution. $^{125}I$ Iodinated streptavidin (Amersham) was diluted 1:2500 in blot solution and incubated with blots for 1 hour, at 2 TCi in a 50 ml incubation volume. Blot sections were then washed with blot solution until the detectable radioactivity in the waste solution decreased to background levels. The blot section was then wrapped in saran wrap and exposed to film overnight with a cronex intensifying screen at −80° C. The IgE binding pattern shown in FIG. 13 demonstrates reactivity to affinity purified TRFP (lane 1) chain 1, 6 KD in molecular weight and chain 2,≧16 KD. The recombinant chain 1 shows strong IgE binding (lane 2) while recombinant chain 2 reactivity is reduced compared to chain 1 (lane 3). The recombitope peptides that show IgE binding are recombitope peptides XYZ and ZXY (lanes 4 and 8 respectively). All other recombitope peptides are negative for IgE binding by this method of analysis.

Specific binding of IgE to recombitope peptides was also demonstrated in ELISA assays. Corning assay plates (#25882-96) were coated with 10 Tg/ml of each coating antigen (i.e., TRFP, chain 1(recombinant chain 1 of TRFP), chain 2 (recombinant chain 2 of TRFP), recombitope peptide XZY, recombitope peptide XZY, recombitope peptide YXZ, recombitope peptide YZX, recombitope peptide ZXY and recombitope peptide ZYX) listed in FIG. 14 at 50 Tl/well and incubated overnight at 4° C. The coating antigens were removed and the wells were blocked with 0.5% gelatin in PBS, 200 Tl/well for 2 hours at room temperature. Plasma from patient #669 was serially diluted with PBS-Tween 20 (PBS with 0.05% nonionic detergent Tween-20 Sigma, St. Louis Mo.) and 100 Tl/well was added and incubated overnight at 4° C. (plasma dilutions are tested in duplicate). The second antibody (biotinylated goat anti-Human IgE, 1:1000, Kirkegaard & Perry Laboratories Inc. Gaithersburg, Md.), was added at 100 Tl/well for one hour at room temperature. This solution was removed and streptavidin-HRPO, 1:10,000 (Southern Biotechnology Associates, Inc., Birmingham, Ala.) was then added at 100 Tl/well for one hour at room temperature (all wells were washed three times with PBS-Tween between each incubation step). TMB Membrane Peroxidase Substrate system (Kirkegaard & Perry Laboratories) was freshly mixed, and added at 100 Tl/well. The color was allowed to develop for 2–5 minutes. The reaction was stopped by the addition of 100 Tl/well of 1M phosphoric acid. Plates were read on a Microplate EL 310 Autoreader (Biotek Instruments, Winooski, Vt.) with a 450 nm filter. The absorbance levels of duplicate wells were averaged. The graphed results (log of the dilution vs absorbance) of the ELISA assays are shown in FIG. 14.

Figure 14:
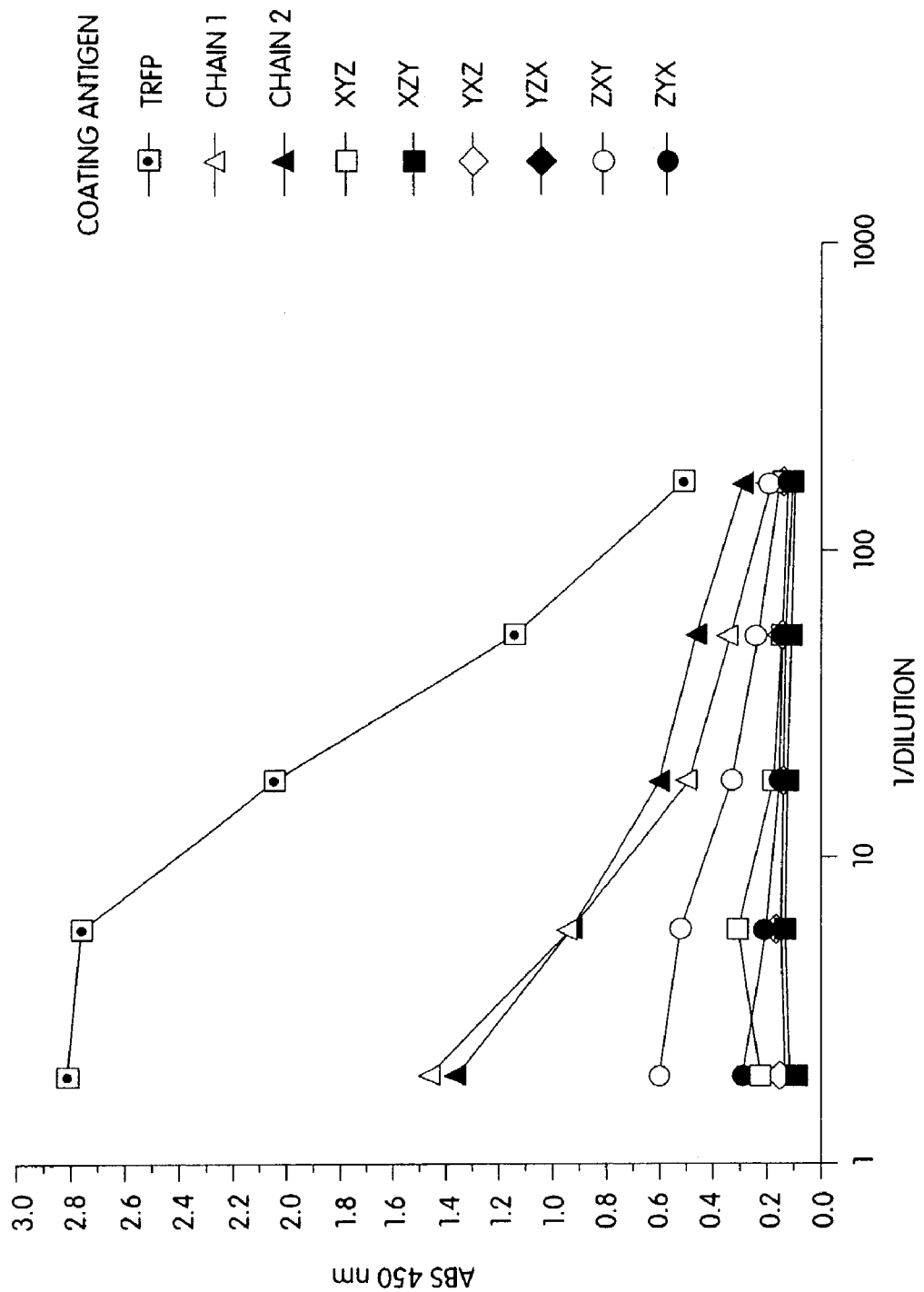
FIG. 14 is a graphic representation of the results of ELISA analysis illustrating the binding of human IgE obtained from a cat allergic individual to various protein samples, including recombitope peptides XYZ, XZY, YXZ, YZX, ZXY, and ZYX.

The results of the ELISA shown in FIG. 14 demonstrate a high level of IgE binding to TRFP with somewhat lower binding to recombinant TRFP chain 1 (chain1) and chain 2 (chain 2). The two recombinant chains demonstrate equivalent binding with this particular patient's IgE. Only the recombitope peptide ZXY shows clear reactivity with IgE. The binding of the other recombitope peptides is at or near the background level with a slight signal from recombitope peptide XYZ. To demonstrate that recombitope peptides were present in equal amounts in both the ELISA and Western assay, anti-peptide antisera was used as a positive control and it gave fairly equivalent signals for all lanes and wells with recombitope peptides.

EXAMPLE 4

HUMAN T CELL EPITOPE RESPONSE TO RECOMBITOPE PEPTIDES

Figure 15A:
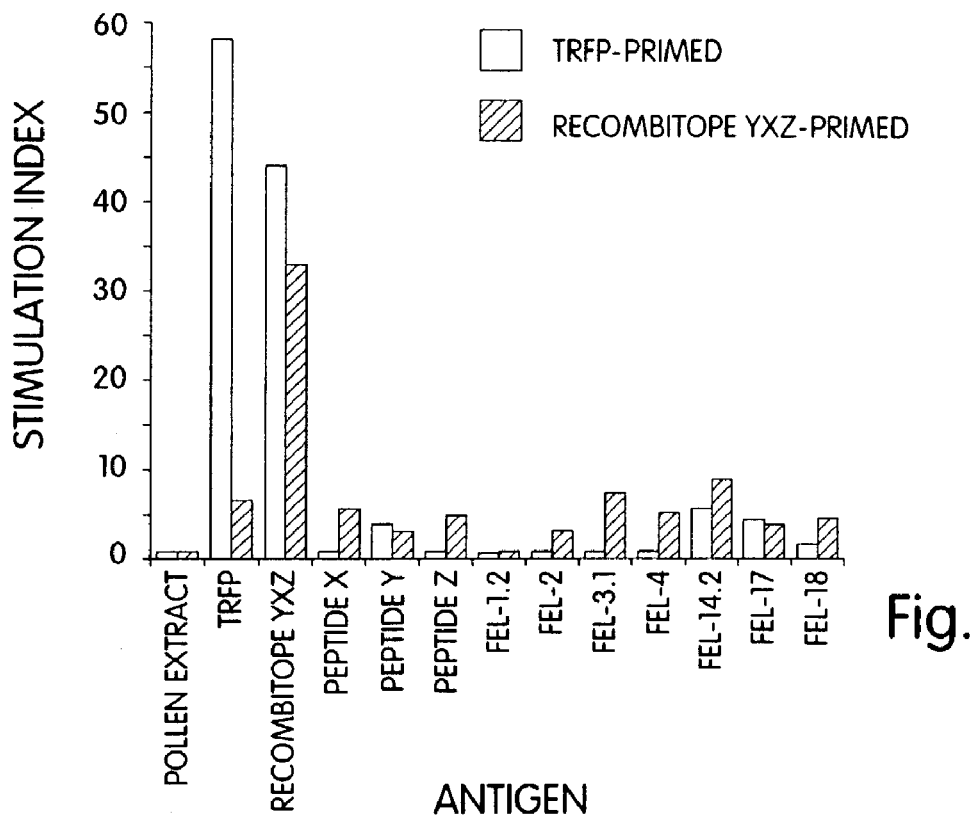
FIG. 15a, 15b and 15c are graphic representations depicting the responses of T cell lines from three patients primed in vitro to TRFP, recombitope peptide YXZ, or recombitope peptide YZX, and analyzed for response to various peptides.
Figure 15B:
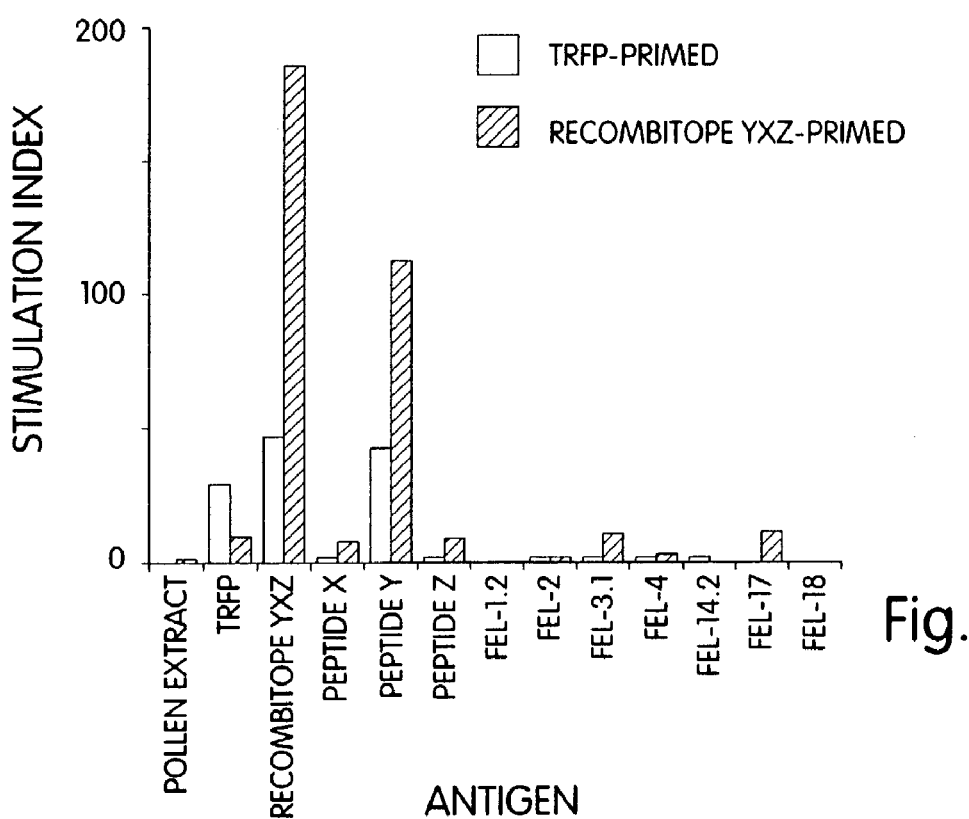
Figure 15C:
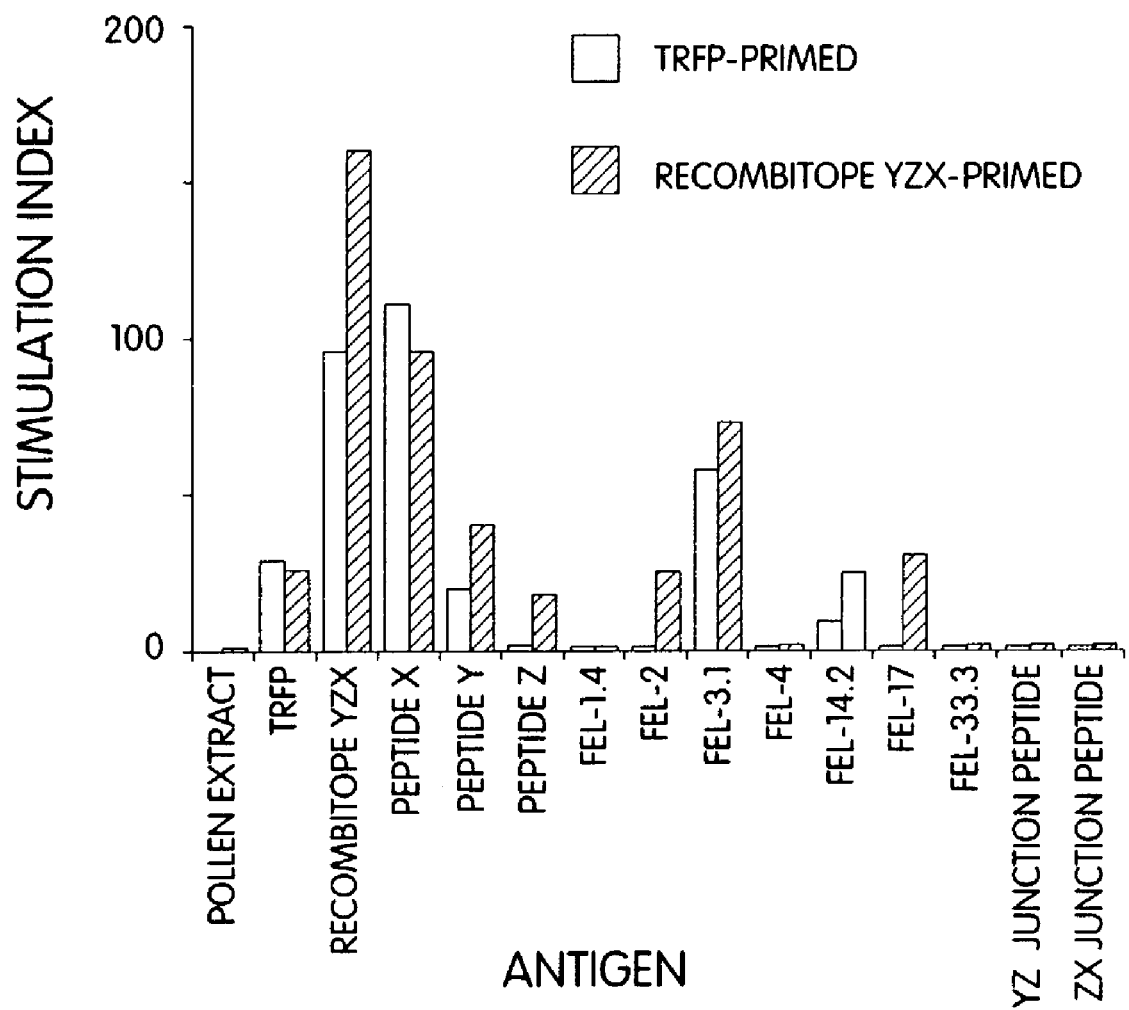

The human cat allergic T cell response to recombitope peptides was examined. Peripheral blood mononuclear cells (PBMC) were purified by Ficoll-Hypaque centrifugation of 60 ml of heparinized peripheral blood from cat-allergic patients, who exhibited clinical symptoms of cat allergy and who were skin test positive with cat extract. Ten million PBMC from an individual patient were cultured in 10 ml RPMI-1640 containing 5% pooled human AB serum and supplemented with glutamine, penicillin, streptomycin and HEPES buffer in the presence of 10 1 g native affinity-purified TRFP/ml of culture or with 25 1 g purified uncleaved recombitope peptide YXZ/ml of culture or with 25 1 g purified cleaved recombitope peptide YZX/ml of culture at 37° C. for 7 days. Recombitope peptide YZX was cleaved with thrombin as described in Example 2. Viable cells were then purified by Ficoll-Hypaque centrifugation and cultured for 2 additional weeks in RPMI-1640/5% AB serum containing 5 units recombinant human IL-2/ml and 5 units recombinant human IL-4/ml. The resting T cells were then tested in a secondary proliferation assay using a 96 well microtiter plate to assess T cell responses to various TRFP proteins or peptides (TRFP antigens). For assay, $2 \times 10^4$ resting T cells were cultured for 3 days at 37° C. in the presence of $2 \times 10^4$ autologous Epstein-Barr virus transformed B cells (25,000 Rads) as antigen presenting cells with various concentrations of antigen in 200 11 per well. Each well then received 11Ci tritiated thymidine for 16 hours. The counts incorporated were collected onto glass fiber filters and processed for liquid scintillation counting. The stimulation indices for responses to each antigen were then calculated as the maximum CPM in response to antigen divided by the medium control CPM. A stimulation index of 2.5 was considered to be a positive T cell response. A summary of the results of 3 such experiments (patients 522, 519, and 386 is shown in FIG. 15a, FIG. 15b and FIG. 15c. As compared to the experiments shown in FIGS. 15a and 15b, in the experiment shown in FIG. 15c, Fel-1.4 (chain 1, amino acid residues 6–17) was substituted for Fel-1.2 (chain 1, amino acid residues 1–17) and Fel-33.3 (chain 2, amino acid residues 26–40) was substituted for Fel-18 (chain 2, amino acid residues 23–48) in order to more closely resemble the constituent amino acids of peptides X and Z. In addition, in this experiment one peptide derived from the Y-Z junction of recombitope peptide YZX (amino acid residues 50–55 from chain 1 of TRFP and amino acid residues 14–19 from chain 2 of TRFP) and one peptide derived from the Z-X junction of recombitope peptide YZX (amino acid residues 34–39 of chain 2 of TRFP and amino acid residues 7–12 of chain 1 of TRFP) were synthesized and tested. These junction peptides were produced in order to determine whether these areas of recombitope peptide YZX produce a non-native epitope when formed in the recombitope peptide.

The results indicate that T cells from patient 522 primed with native TRFP positively respond to native TRFP, recombitope peptide YXZ, peptide Y, Fel-14.2 and Fel-17. In contrast, T cells primed with recombitope YXZ respond less well to native TRFP, but respond at a similar level or better to a number of synthetic peptides corresponding to portions of the TRFP molecule, including peptide X, peptide Y, peptide Z, Fel-4, Fel-3.1, Fel-2, Fel-14.2, Fel-17 and Fel-18. Similar results of an experiment with T cells from patient 519 are shown in FIG. 15b. Native TRFP-primed T cells from this patient respond to native purified TRFP, recombitope peptide YXZ and peptide Y. When the same patient's cells were primed with recombitope peptide YXZ, positive responses were shown to native TRFP, recombitope peptide YXZ, peptide X, peptide Y, peptide Z, Fel-3.1, Fel-4, and Fel-17. FIG. 15c shows a similar experiment involving purified cleaved recombitope YZX as the priming antigen. The results indicate that T cells from patient 386 primed with native TRFP positively respond to native TRFP, recombitope peptide YZX, peptide X, peptide Y, Fel-3.1, and Fel-14.2. In contrast, T cells primed with recombitope YZX respond at a similar level or better to native TRFP, recombitope peptide YZX, peptide X, peptide Y, peptide Z, Fel-2, Fel-3.1, Fel-14.2 and Fel-17. These data indicate that, at least in these three patients, T cells can efficiently recognize TRFP T cell epitopes when presented as a recombitope peptide. No epitopes present in the native TRFP molecule examined in these experiments are destroyed in the context of the YXZ recombitope peptide. The ability of the recombitope peptides YXZ or YZX to present TRFP epitopes in these experiments appears to be greater compared with the native molecule. The results from Patient 386 demonstrate that peptides derived from the junctional areas of the recombitope YZX (YZ junction peptide and ZX junction peptide) are not recognized by T cells when presented in a recombitope peptide; therefore, no non-native epitopes are created in the junctional areas.

EXAMPLE 5

MURINE T CELL RESPONSE TO RECOMBITOPE PEPTIDES

Mice were immunized with recombitope peptide YZX to determine whether T cell epitopes contained in the recombitope peptide derived from TRFP are capable of stimulating a T cell response. The assay determined the ability of lymph node cells to respond to the individual recombitope peptides as well as the immunizing antigen.

10 B6CBAF1 mice were immunized subcutaneously at the base of the tail and in the thigh region with 100 1 g of recombitope peptide YZX in complete Freund's adjuvant. After 10 days, the inguinal, paraaortic, and popliteal nodes of the immunized mice were removed and pooled. The lymph node cells were suspended in cold RPMI 1640 with 1% fetal bovine serum (FBS) by passage through stainless steel mesh. The cells were washed 2 times with cold RPMI-1640 containing 1% FBS and maintained at 4° C.

Figure 16:
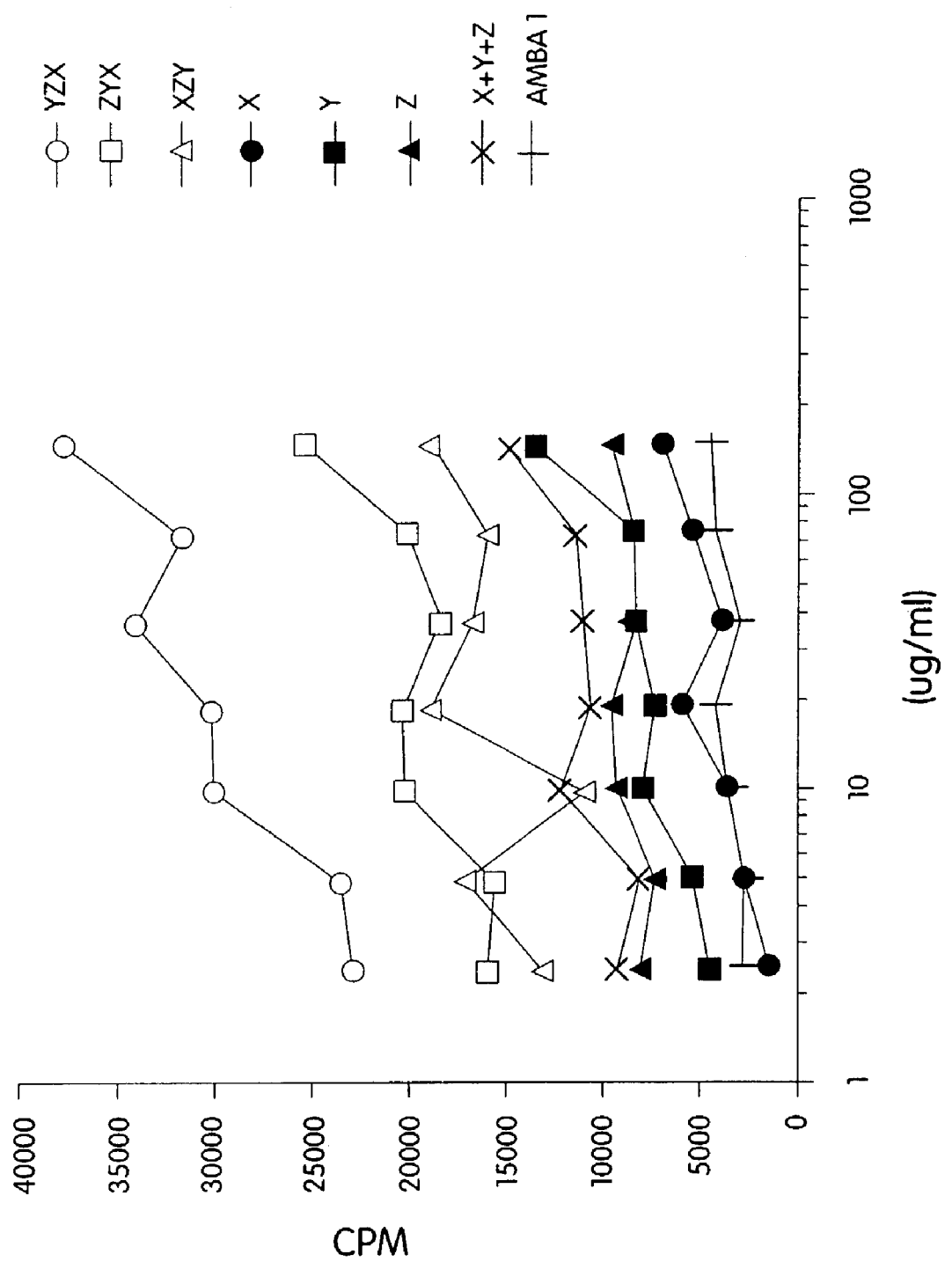
FIG. 16 is a graphic representation depicting responses of murine T cells immunized with recombitope peptide YZX and analyzed for response in vitro to culture with the recombitope peptide YZX as measured by IL-2 production.

The lymph node cells were plated at $4 \times 10^6$ cells/ml in RPMI 1640 with 10% FBS, 250 1 g/ml penicillin G, 100 1 g/ml streptomycin, and $5 \times 10^{-5}$ M 2-mercaptoethanol. The cells were cultured with antigen (i.e., recombitope peptide YZX, recombitope peptide ZYX, recombitope peptide XZY, peptide X, peptide Y, peptide Z, peptides X, Y and Z and Amb a I) as indicated (FIG. 16). After 24 hours, 50 11 of supernatant was removed from each culture and frozen overnight to eliminate live cell carryover. The supernatant was warmed to 37° degrees and washed. CTLL-2 indicator cells (ATCC # T1B 214) were added ($5 \times 10^3$ cells/well). This indicator cell line requires IL-2 for continued growth. After 24 hours, $H^3$-thymidine (11 Ci/well) was added and the cells were further incubated for 4 hours. The plates were frozen and thawed, harvested on a Tomtec 96 well harvester (Tomtec, Orange, Conn.), and counted on a Betaplate beta counter (Pharmacia, Gaithersburg, Md.).

The pooled lymph node cells respond well in vitro in response to culture with recombitope peptide YZX, as measured by IL-2 production (FIG. 16). The media only background averaged 1500 cpm. The T cell response to recombitope peptide YZX may result from one or a combination of responses to the individual peptide containing epitopes used to construct the recombitope peptide (i.e., peptides X, Y and Z). Other recombitope peptides as well as the individual peptides X, Y and Z were cultured with lymph node cells and the response of T cells was determined. There was significant response to each of the peptides X, Y and Z, the constituent peptides. There were strong T cell responses to several other recombitope peptides ZYX and XZY. There was a small, but significant, T cell response to a recombinant Amb a I preparation which has the same amino-terminal leader sequences as the recombitope peptides.

EXAMPLE 6

APPLICATION OF RECOMBITOPES TO ALLERGIC DISEASE DIAGNOSIS

The recombitope peptides can be useful as a new form of diagnosis of sensitivity to a protein allergen or a protein antigen. For example, although preferred recombitope peptides of the invention do not bind IgE, certain recombitope peptides derived from protein allergens may be capable of binding allergic patient IgE. These recombitope peptides could be used in skin testing as an accurate assay for specific Immediate Type Hypersensitivity (ITH) in an individual to the protein allergen from which the recombitope peptide is derived. The allergens for eliciting the ITH response could also be recombinant produced allergens, biochemically purified allergens from natural sources in addition to recombitope peptides with the only requirement being a high degree of specific IgE reactivity. Recombitope peptides which show no, or very low, reactivity with human IgE but comprise T cell epitopes reactive with a protein allergen can be used to elicit a Delayed Type Hypersensitivity (DTH) reaction in an individual sensitive to the allergen from which the epitopes are derived. The allergen forms for generating the DTH response can be isolated recombitope peptides, recombinant allergens or chemically modified natural or recombinant allergens (e.g., KOH treated TRFP). Again, a major requirement of the DTH provoking allergen/antigen is lack of IgE binding reactivity, or if such binding occurs, lack of mediator release from mast cells or basophils and the ability to stimulate T cells in an individual upon administration. A positive DTH is indicative of T cells of the individual specific for the epitopes within the recombitope peptide. In general, recombitope peptides are larger molecules than peptides which comprise an individual T cell epitope and are thus advantageous for DTH testing. Since the recombitope peptides are larger molecules, it is believed that they should reside in the skin (site of injection) allowing for the influx of T lymphocytes and other cells that contribute to the DTH skin response.

The ITH reaction, which occurs within 15 to 30 minutes of skin testing, can be used in combination with a DTH reaction, with the DTH reaction appearing 48–72 hours later. It is the combination of these assays, for two different types of allergic disease related reactivities, that represents a novel diagnostic formulation. The application to the skin during skin testing with a recombitope peptide may require a different format for eliciting one response versus another (ITH vs DTH). For example, the ITH reaction may be elicited in an individual by prick testing with a very small quantity of a therapeutic composition comprising a recombitope peptide (in this case the an IgE reactive recombitope peptide), and a pharmaceutically acceptable carrier or diluent. To elicit a DTH reaction, a large amount of a therapeutic composition comprising a recombitope peptide (in this case a non-IgE reactive recombitope peptide) and a pharmaceutically acceptable carrier or diluent is applied by an intradermal injection or tine test form (both are used for TB testing by DTH). See *Immunology* (1985) Roitt, I. M., Brostoff, J., Male, D. K. (eds), C. V. Mosby Co., Gower Medical Publishing, London, N.Y., pp. 19.2–19.18; pp. 22.1–22.10.

Following diagnosis with recombitope peptides of the invention individuals can be selected for specific desensitization therapy by defining, in one test set, IgE reactivity and T epitope reactivity.

The invention claimed is:

1. A method for designing an isolated peptide having an amino terminus and a carboxy terminus comprising at least two regions each having human T cell stimulating activity, wherein said regions comprise an epitope of a protein allergen selected from one or both of *Dermatophagoides pteronyssinus* I (Der p I) and *Dermatophagoides pteronyssinus* II (Der p II), and wherein said regions are arranged from the amino terminus to the carboxy terminus in a different order than the regions in the naturally-occurring protein allergen, comprising the steps of:
   a) dividing amino acid sequence of the protein allergen into at least two regions;
   b) determining whether the regions of step (a) have T cell stimulating activity;
   c) arranging the regions to form at least one peptide in which the regions are arranged from the amino terminus to the carboxy terminus in a different order than the regions in the naturally-occurring protein allergen; and
   d) producing at least one peptide having the arrangement of the regions of step (c).

2. The method of claim 1, further comprising the step of determining whether the peptide of step (d) has T cell stimulating activity.

3. The method of claim 1, further comprising the step of determining whether the peptide binds immunoglobulin E specific for the protein allergen of step (a).

4. The method of claim 1, wherein in step (a) the protein allergen is divided into overlapping regions.

5. The method of claim 1, wherein at least one T cell epitope of the protein allergen is known and utilized as at least one of said regions.

6. The method of claim 1, wherein step (b) further comprises determining whether said regions bind immunoglobulin E specific for the allergen of step (a) and cause the release of mediators from mast cells or basophils.

7. The method of claim 1, wherein the peptide is produced recombinantly.

8. The method of claim 1, wherein the peptide is produced synthetically.

9. The method of claim 1, wherein the peptide further comprises a proteolytic site inserted between at least two of said regions.

10. The method of claim 1, wherein each region comprises at least two T cell epitopes of the protein allergen.

11. The method of claim 1, wherein each region comprises at least about thirty amino acid residues of the protein allergen.

12. The method of claim 1, wherein the peptide comprises at least about forty amino acid residues of the protein allergen.

13. The method of claim 1, wherein the peptide comprises at least about fifteen per cent of the T cell epitopes of the protein allergen.

14. The method of claim 1, wherein the peptide comprises at least about thirty per cent of the T cell epitopes of the protein allergen.

15. A method for designing an isolated peptide having an amino terminus and a carboxy terminus comprising at least two regions each having human T cell stimulating activity, wherein each region comprises an amino acid sequence selected from the group consisting of sequence X (SEQ ID NO: 7), sequence Y (SEQ ID NO: 8), sequence Z (SEQ ID NO: 9), sequence A (SEQ ID NO: 10), and sequence B (SEQ ID NO: 11), and wherein said regions are arranged from the amino terminus to the carboxy terminus in a different order than the regions in the naturally-occurring protein allergen, comprising the steps of:
   a) dividing the protein allergen into at least two regions;
   b) determining whether the regions of step (a) have T cell stimulating activity;
   c) arranging the regions to form at least one peptide in which the regions are arranged from the amino terminus to the carboxy terminus in a different order than the regions in the naturally-occurring protein allergen; and
   d) producing at least one peptide having the arrangement of the regions of step (c).

* * * * *